United States Patent
Yamaguchi et al.

(10) Patent No.: US 8,492,172 B2
(45) Date of Patent: Jul. 23, 2013

(54) PARTICLE DETECTION SENSOR, METHOD FOR MANUFACTURING PARTICLE DETECTION SENSOR, AND METHOD FOR DETECTING PARTICLE USING PARTICLE DETECTION SENSOR

(75) Inventors: Mayumi Yamaguchi, Kanagawa (JP); Konami Izumi, Kanagawa (JP); Fuminori Tateishi, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 415 days.

(21) Appl. No.: 12/609,328

(22) Filed: Oct. 30, 2009

(65) Prior Publication Data
US 2010/0141278 A1    Jun. 10, 2010

Related U.S. Application Data

(62) Division of application No. 11/467,320, filed on Aug. 25, 2006, now Pat. No. 7,610,794.

(30) Foreign Application Priority Data
Aug. 26, 2005    (JP) ................ 2005-246554

(51) Int. Cl.
*H01L 21/00*    (2006.01)
*H01L 27/14*    (2006.01)

(52) U.S. Cl.
USPC .......... 438/5; 438/6; 438/14; 438/48; 438/50; 257/252; 257/414; 250/282; 250/288; 324/691; 324/693

(58) Field of Classification Search
USPC ................ 438/5, 6, 14, 48–50; 257/252, 253, 257/414, 416; 324/691, 693, 696; 250/282, 250/288
See application file for complete search history.

(56) References Cited

U.S. PATENT DOCUMENTS

| | | | |
|---|---|---|---|
| 4,323,843 A | 4/1982 | Batham | |
| 4,647,364 A | 3/1987 | Mase | |
| 5,056,355 A | 10/1991 | Hepher | |
| 5,082,242 A * | 1/1992 | Bonne et al. | 251/129.01 |
| 5,247,827 A | 9/1993 | Shah | |
| 5,384,535 A | 1/1995 | Mayeur | |
| 5,457,396 A | 10/1995 | Mori | |
| 5,910,700 A | 6/1999 | Crotzer | |

(Continued)

FOREIGN PATENT DOCUMENTS

| | | |
|---|---|---|
| DE | 101 33 385 C1 | 1/2003 |
| EP | 0766086 A2 | 4/1997 |

(Continued)

*Primary Examiner* — Hsien Ming Lee
(74) *Attorney, Agent, or Firm* — Fish & Richardson P.C.

(57) ABSTRACT

A compact sensor with which particles floating in the air can be easily detected. A sensor having a microstructure which detects a detection object by contact is used. A microstructure has an opening to be a detection hole corresponding to the size of a detection object, and a pair of electrodes having a bridge structure are provided thereabove or thereunder so as to partially contact with each other.

20 Claims, 17 Drawing Sheets

U.S. PATENT DOCUMENTS

| | | |
|---|---|---|
| 6,210,972 B1 | 4/2001 | Williams |
| 6,634,210 B1 | 10/2003 | Bosch |
| 6,668,616 B1 | 12/2003 | Shoji |
| 6,940,564 B2 * | 9/2005 | Murden et al. .................. 349/1 |
| 7,081,623 B2 * | 7/2006 | Pai et al. ...................... 250/299 |
| 7,144,496 B2 | 12/2006 | Meserol |
| 7,501,739 B2 * | 3/2009 | Itaya et al. .................... 310/320 |
| 2002/0042965 A1 | 4/2002 | Salem |
| 2002/0194919 A1 * | 12/2002 | Lee et al. ........................ 73/718 |
| 2005/0248232 A1 * | 11/2005 | Itaya et al. .................... 310/320 |
| 2007/0119233 A1 | 5/2007 | Schnell |
| 2007/0158191 A1 | 7/2007 | Berger |

FOREIGN PATENT DOCUMENTS

| | | |
|---|---|---|
| JP | 61089541 A | 5/1986 |
| JP | 07-083830 | 3/1995 |
| JP | 09138192 A | 5/1997 |
| JP | 2000310608 A | 11/2000 |
| JP | 2002-157511 | 5/2002 |
| JP | 2003-329704 | 11/2003 |
| JP | 2005010083 A | 1/2005 |
| TW | 520521 B | 2/2003 |
| WO | 01/93304 A1 | 12/2001 |
| WO | WO 2006/094923 | 9/2006 |

* cited by examiner

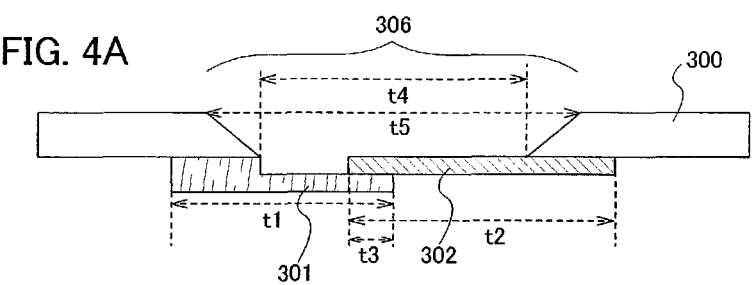
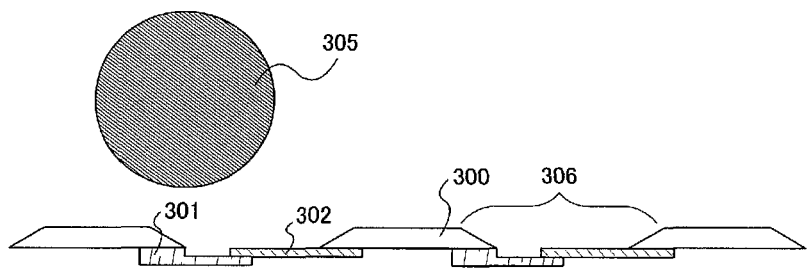
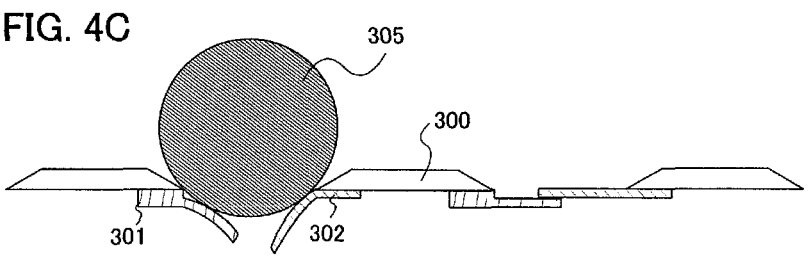

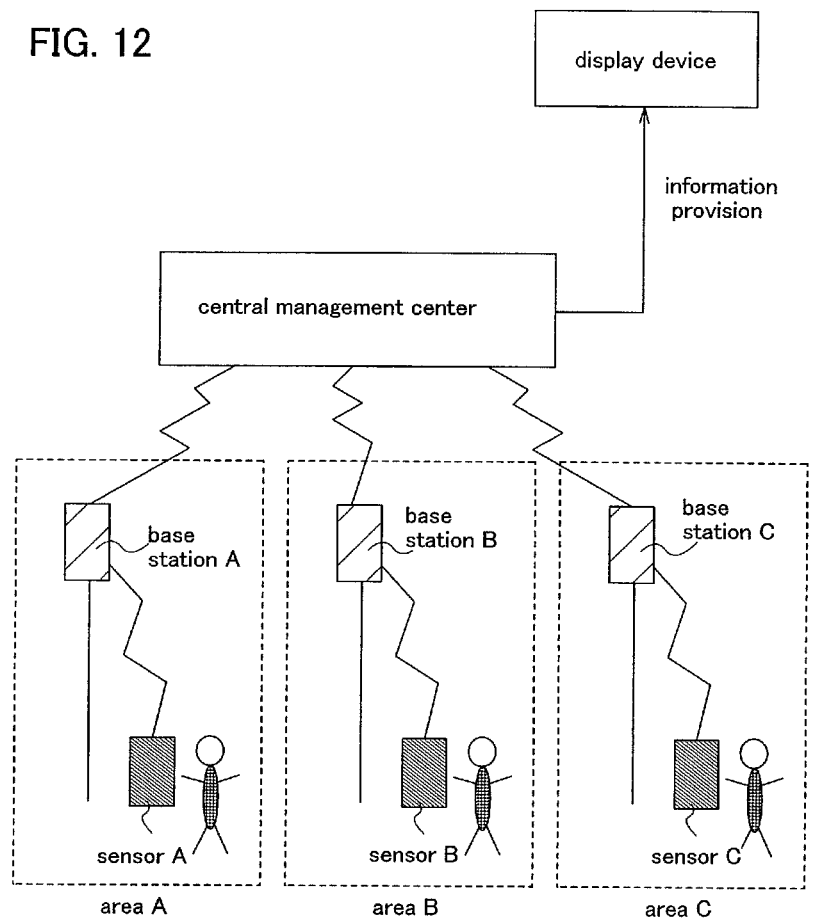

PARTICLE DETECTION SENSOR, METHOD FOR MANUFACTURING PARTICLE DETECTION SENSOR, AND METHOD FOR DETECTING PARTICLE USING PARTICLE DETECTION SENSOR

CROSS-REFERENCE TO RELATED APPLICATIONS

This application is a divisional of U.S. application Ser. No. 11/467,320, filed Aug. 25, 2006, now U.S. Pat. No. 7,610,794, which claims the benefit of a foreign priority application filed in Japan as Serial No. 2005-246554 on Aug. 26, 2005, both of which are incorporated by reference.

BACKGROUND OF THE INVENTION

1. Field of the Invention

The preset invention relates to a sensor for detecting particles through a MEMS technology, a method for manufacturing such a sensor, and a method for detecting particles using a particle detection sensor.

2. Description of the Related Art

Research on micromechanical systems called MEMS has been actively advanced. MEMS (Micro Electro Mechanical System) is an abbreviation of a microelectromechanical system, and also simply called a micromachine. A micromachine means a microdevice formed by integrating a "movable microstructure with a three-dimensional structures" using a semiconductor micromachining technique. A microstructure may function as a switch, a variable capacitor, an actuator, or the like. Such a micromachine is formed from a silicon wafer, and is used as an inertial force sensor (Reference 1: Japanese Patent Application Publication No. 2003-329704).

As an example of a sensor used at present, a pollen sensor can be given. The number of hay fever sufferers continues to increase, and hay fever (pollinosis) assumes a national disease. If exposure to pollen can be reduced, it is considered that development of pollinosis can be reduced. In order to reduce exposure to pollen, it is effective to grasp the amount of pollen dispersed and avoid area where much pollen is dispersed. As a method of grasping the amount of dispersed pollen, a system for collecting pollen information by measuring the amount of pollen dispersed in the air is proposed (Reference 2: Japanese Patent Application Publication No. 2002-157511).

As a pollen sensor, a structure including a light source which emits excitation light and a detector which detects luminescence emitted by pollen exposed to the excitation light is proposed (Reference 3: Japanese Patent Application Publication No. 7-83830).

SUMMARY OF THE INVENTION

Since a conventional pollen sensor performs detection in an optical manner, there has been a problem that long time is required for the measurement. Further, it has also been a problem that a light source or a detector is required to be used, and the device has become larger. Meanwhile, in view of a pollution problem such as atmospheric pollution in addition to familiar problems such as hay fever, a means for easily detecting particles floating in the air has been required.

Correspondingly, it is an object of the present invention to provide a sensor with which particles floating in the air can be easily detected. Further, it is another object of the invention to provide such a particle detection sensor at low cost.

In order to solve the above problems, a particle detection sensor of the invention has a detector which detects a detection object by physical contact or noncontact of a pair of electrodes. The detector preferably has a detecting element having a microstructure. In addition, a particle detection sensor of the invention is preferably formed of a thin film material over an insulating substrate.

A detecting element has an opening to be a detection hole corresponding to the size of a detection object, and a pair of electrodes are provided thereabove or thereunder so as to partially contact with each other. When the detection object is adsorbed to the detection hole, the pair of electrodes are detached from each other, in other words, are out of a non-contact state. By determining whether the pair of electrodes are in contact or not (in a non-contact state), the presence or absence of the detection object can be detected. On the other hand, the pair of electrodes may be first apart from each other. The presence or absence of the detection object can be detected even in the case of a structure in which a detection object is adsorbed to the detection hole, and the pair of electrodes contact accordingly. Note that, the pair of electrodes preferably has a bridge structure. The bridge structure means, for example, a structure formed over a substrate, either ends of the structure being fixed to the substrate and a center of the structure not contacting the substrate, or the structure being partially fixed to the substrate and the other part not contacting the substrate.

A particle detection sensor of the invention has a detector including such a detecting element and a circuit with which the presence or absence of the detection object can be determined. Note that, the detecting element preferably has a microstructure. In the present invention, a microstructure forming a part of a detecting element which detects a detection object and a semiconductor element which controls the detecting element can be manufactured over one insulating substrate. In addition, a circuit which determines the presence or absence of the detection object can also be formed over the same insulating substrate over which the microstructure is formed. Note that an insulating substrate refers to a substrate having an insulating surface, while includes a substrate in which a conductive substrate material is covered with an insulating material.

A particle detection sensor of the invention has intake unit for making a detection object adsorbed to a detection hole. In order to make the detection object be adsorbed, reduced pressure is preferable. Under reduced pressure, the adsorption ratio of the detection object can be increased and the accuracy of capturing the detection object can be increased.

Specific modes of the present invention will be described below.

One mode of the present invention is a particle detection sensor including a detector having a base provided with an opening and a pair of electrodes provided in a path of an air current flowing into the opening in such a manner that the pair of electrodes can be electrically in contact. The detector detects a detection object by determining whether the pair of electrodes are electrically in contact or out of contact.

Another mode of the present invention is a particle detection sensor including a detecting element having a base provided with an opening and a detecting element having a pair of electrodes provided in a path of an air current flowing into the opening in such a manner that the pair of electrodes can be electrically in contact, and a circuit which determines whether the pair of electrodes are electrically in contact or out of contact.

Another mode of the present invention is a particle detection sensor including a detector having an insulating layer; a pair of electrodes provided over the insulating layer in such a manner that the pair of electrodes can be electrically in contact; and a base having an opening provided over the pair of electrodes. The detector detects a detection object by determining whether the pair of electrodes are electrically in contact or out of contact.

Another mode of the present invention is a particle detection sensor which has a detecting element including: an insulating layer, a pair of electrodes provided over the insulating layer in such a manner that the pair of electrodes can be electrically in contact, and a base having an opening provided over the pair of electrodes; and a circuit which determines whether the pair of electrodes are electrically in contact or out of contact.

In a particle detection sensor of the present invention, the particle detection sensor can have an intake unit for reducing pressure in the opening, which is connected to the opening.

In a particle detection sensor of the present invention, the particle detection sensor can include a communication device.

In a particle detection sensor of the present invention, wherein a pair of electrodes provided over the insulating layer in such a manner that the pair of electrodes can be electrically in contact and openings may be arranged in matrix, and the particle detection sensor can be an active type in which a switching element is provided on each of the openings or a passive type in which switching elements are not provided on every opening.

In a particle detection sensor of the present invention, the pair of electrodes which are provided in such a manner that the pair of electrodes can be electrically in contact may have a bridge structure. Note that a bridge structure means, for example, a structure formed over a substrate, either ends of the structure being fixed and a center of the structure not contacting the substrate, or the structure being partially fixed to the substrate and the other part not contacting the substrate.

A method for manufacturing a particle detection sensor of the present invention includes the steps of: forming an insulating layer; forming a first electrode over the insulating layer; forming a second electrode so as to overlap with a part of the first electrode; and forming an opening in the insulating layer at a region where the first electrode and the second electrode overlap.

A method for manufacturing a particle detection sensor of the present invention includes the steps of: forming a semiconductor layer in a first region; forming an insulating layer in the first region and a second region; forming a first electrode in the second region over the insulating layer; forming a second electrode so as to overlap with a part of the first electrode; and forming an opening in the insulating layer at a region where the first electrode and the second electrode overlap.

11. A method for manufacturing a particle detection sensor of the present invention includes the steps of: forming an insulating layer; forming a first electrode over the insulating layer; forming a sacrificial layer over the first electrode; forming a second electrode over the sacrificial layer so as to overlap with a part of the first electrode; forming an opening at a region where the first electrode and the second electrode overlap in the insulating layer; and removing the sacrificial layer.

A method for manufacturing a particle detection sensor of the present invention includes the steps of: forming an insulating layer; forming a first electrode over the insulating layer; forming a sacrificial layer over the first electrode; forming a second electrode over the sacrificial layer so as to overlap with a part of the first electrode; and forming an opening at a region where the first electrode and the second electrode overlap in the insulating layer. The first electrode and the second electrode are in contact with each other when the sacrificial layer is removed.

13. A method for manufacturing a particle detection sensor of the present invention includes the steps of: forming a sacrificial layer over the first electrode; forming a conductive layer in the first region and a second region; processing the conductive layer thereby forming a gate electrode in the first region and forming a first sacrificial layer in the second region; forming an insulating layer so as to cover the gate electrode and the first sacrificial layer; forming a first electrode over the insulating layer; forming a second sacrificial over the first electrode; forming a second electrode over the second sacrificial layer so as to overlap with a part of the first electrode; and forming an opening at a region where the first electrode and the second electrode overlap in the insulating layer. The first electrode and the second electrode are in contact with each other when the sacrificial layer is removed, and the first sacrificial layer is removed.

A method for manufacturing a particle detection sensor of the present invention includes the steps of: forming a sacrificial layer over the first electrode; forming a conductive layer in the first region and a second region; processing the conductive layer thereby forming a gate electrode in the first region and forming a first sacrificial layer in the second region; forming an insulating layer so as to cover the gate electrode and the first sacrificial layer; forming a first electrode over the insulating layer; forming a second sacrificial over the first electrode; forming a second electrode over the second sacrificial layer so as to overlap with a part of the first electrode; and forming an opening at a region where the first electrode and the second electrode overlap in the insulating layer. The first electrode and the second electrode are in contact with each other when the sacrificial layer is removed, and the first sacrificial layer is removed thereby forming a connection hole.

In the present invention, the sacrificial layer can be removed by dry etching or wet etching. Further, the opening can be formed by dry etching or wet etching.

A detection method of the present invention uses a particle detection sensor having a detector including a base provided with an opening and a pair of electrodes provided in a path of an air current flowing into the opening in such a manner that the pair of electrodes can be electrically in contact, which detects a detection object by determining whether the pair of electrodes are electrically in contact or out of contact. The number of detection objects is counted using a state where the pair of electrodes are in contact and a state where the pair of electrodes are detached when detection objects are adsorbed to the opening.

A detection method of the present invention uses a particle detection sensor having an intake unit and a detector including a base provided with an opening and a pair of electrodes provided in a path of an air current flowing into the opening in such a manner that the pair of electrodes can be electrically in contact, which detects a detection object by determining whether the pair of electrodes are electrically in contact or out of contact. The number of detection objects is counted using a state where the pair of electrodes are in contact and a state where pressure is reduced by the intake unit and the pair of electrodes are detached when detection objects are adsorbed to the opening.

A detection method of the present invention uses a particle detection sensor having a detector including a base provided with an opening and a pair of electrodes provided in a path of an air current flowing into the opening in such a manner that the pair of electrodes can be electrically in contact, which detects a detection object by determining whether the pair of electrodes are electrically in contact or out of contact. The number of detection objects is counted using a state where the pair of electrodes are detached and a state where the pair of electrodes are in contact when detection objects are adsorbed to the opening.

A detection method of the present invention uses a particle detection sensor having an intake unit and a detector including a base provided with an opening and a pair of electrodes provided in a path of an air current flowing into the opening in such a manner that the pair of electrodes can be electrically in contact, which detects a detection object by determining whether the pair of electrodes are electrically in contact or out of contact. The number of detection objects is counted using a state where the pair of electrodes are detached and a state where pressure is reduced by the intake unit and the pair of electrodes are in contact when detection objects are adsorbed to the opening.

In the present invention, the detector includes a detection element having the base and the pair of electrodes, and a resistance value of the detection element in the state where the pair of electrodes are in contact is lower than a resistance value in the state where the pair of electrodes are detached, and the number of the detection objects is counted using relative change in the resistance values.

The invention can provide a particle detection sensor using a microstructure formed of a thin film material over an insulating substrate. The invention using a microstructure formed of a thin film material without using an optical method is a compact (small size) particle detection sensor of which measurement time is short.

In accordance with the present invention, since a particle detection sensor is formed using a thin film material over an insulating substrate, a low-cost particle detection sensor can be provided.

BRIEF DESCRIPTION OF DRAWINGS

In the accompanying drawings:

FIGS. 4A to 4C are figures illustrating operation of a switch of the present invention;

FIG. 12 is a figure illustrating the use of a detection unit of the present invention;

DETAILED DESCRIPTION OF THE INVENTION

Embodiment Modes

Figure 1A:
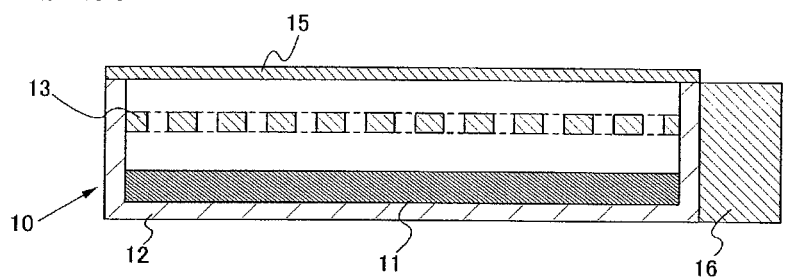
FIGS. 1A and 1B are figures illustrating a structure of a particle detection sensor of the present invention.

Embodiment Modes will be described below with reference to the drawings. However, the present invention is not limited to the description below because it is easily understood by those skilled in the art that the modes and details can be variously modified without departing from the sprit and scope of the invention. Therefore, the present invention should not be construed as being limited thereto. Incidentally, in the descriptions for explaining the structure of the invention with reference to drawings, the same reference numerals denoting the same parts or parts having the same functions are commonly used in the different drawings.

Embodiment Mode 1

In this embodiment mode, a structure of a detection unit of a particle detection sensor will be described.

FIG. 1A shows a cross-sectional view of a detection unit. In a detection unit 10, a detector 11 is provided in a receptacle 12 and a filter 13 is provided above the detector 11. A detection object can be detected using the detector 11. Hereupon, a detection hole is provided on the detector 11, and the detection is preferably conducted when the detection object is adsorbed to the detection hole. Further, articles which are larger than the detection object are prevented from mixing in with the use of the filter 13. In order to increase detection accuracy, the detection unit is preferably used in such a manner that a cover 15 is provided on a top face of the receptacle 12 and the cover 15 is removed immediately before the use. Further, the cover 15 is preferably attached also in order to prevent attachment of foreign matter when carried and prevent a sensor area from breaking. The detector 11 can be protected by the receptacle 12 and the cover 15. Such attachment of the cover 15 to the receptacle 12, namely, packaging of the detection unit 10 is preferably conducted under a clean environment as in a clean room in order to prevent foreign matter from mixing in. The mode of the cover 15 is not limited as long as it can cover the filter 13 provided on the receptacle 12. For example, a seal tape or a metal film which have low adhesion force and are easily peeled off, or a thin plate which is provided removably may be used to form the cover 15.

In addition, a connection portion 16 is provided on the side surface of the receptacle 12. A particle detection sensor of the invention can have an intake unit connected to the detection unit 10 with the connection portion 16. Reduced pressure can be kept in the sensor using the intake unit, and thus, the detection object can be adsorbed to the detection hole accurately. In order to make the detection object adsorbed to the detection hole, the sensor may be rotated to cause adsorption by inertia force, or wind load may be applied to the detection hole to cause adsorption. In other words, an air current may be generated by the intake unit so that an object flows into the detection hole.

Figure 1B:
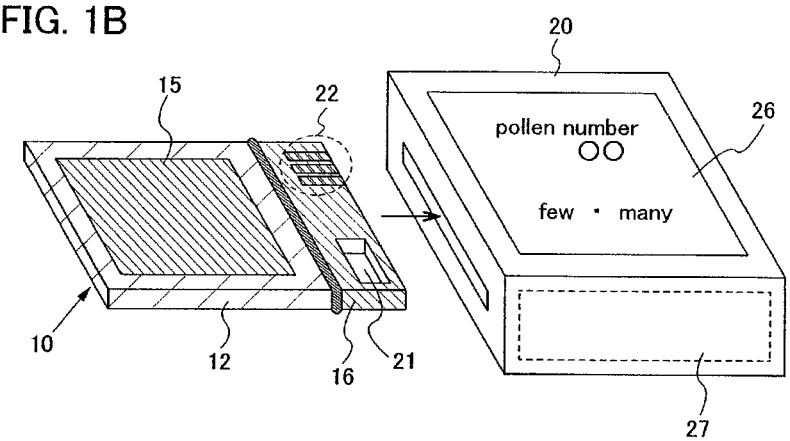

As shown in FIG. 1B, the connection portion 16 is provided with a hole (connection hole) 21 reaching the receptacle 12 and a connection region 22 for making an electrical connection. The connection portion 16 may be provided with an O-ring or the like so as to connect the detection unit 10 and an intake unit 20. The intake unit 20 may have a display area 26 or an arithmetic logical unit (ALU) 27. The display area 26 can display a detection result, an operation method, or the like. The compilation of the detection result or the setting of detection conditions can be performed using the arithmetic logical unit (ALU) 27.

The detection unit 10 is connected to the intake unit 20, the air containing detection objects is taken in over a period of time, and the number of the detection objects can be counted during that time. Foreign particles are removed first using the filter 13 from the air taken in by the intake unit 20. Therefore, the coarseness of the filter 13 is set so as to pass detection objects, for example, at 100 μm to 1 mm. Here, a stack of a plurality of filters which have different coarsenesses in the range of 100 μm to 1 mm may be provided.

The detection objects contained in the air which has passed through the filter 13 are captured by the detector 11, and the number thereof can be detected. Since the number of the detection objects per unit area is preferably detected, the intake unit may preferably be operated for a constant time per measurement to obtain comparable back pressure. Thus, the time for taking the air containing detection object is desirably constant per measurement, and a timer may be provided. For example, a counter circuit is provided on the arithmetic logical unit (ALU) 27 of the intake unit 20, and the constant time can be measured.

Since the detection unit 10 shown in FIGS. 1A and 1B is independent of the intake unit 20, the detection unit 10 can be replaced easily. Specifically, the detector 11 is removable and a used one can be replaced with a new one. Alternatively, a used one may be cleaned to be reused.

The intake unit 20 may be operated by incorporating a primary battery or a secondary battery instead of being connected to a domestic AC power. Alternatively, the intake unit may be operated by being connected to a direct current (DC) power supply of about 6 V to 24 V, which is mounted on a vehicle.

Thus, a particle detection sensor including a detection unit having a detector and an intake unit can be obtained.

In this embodiment mode, the detection unit 10 and the intake unit 20 are separated; however, an intake function may be provided on the detection unit, or in addition, a display function may be provided. In the present invention, a MEMS structure is used for a detector of a detection unit, and other structures are not limited.

Embodiment Mode 2

In this embodiment mode, a case of providing a wireless communication function on a particle detection sensor, for example on an intake unit so as to perform wireless communication will be described.

Figure 11A:
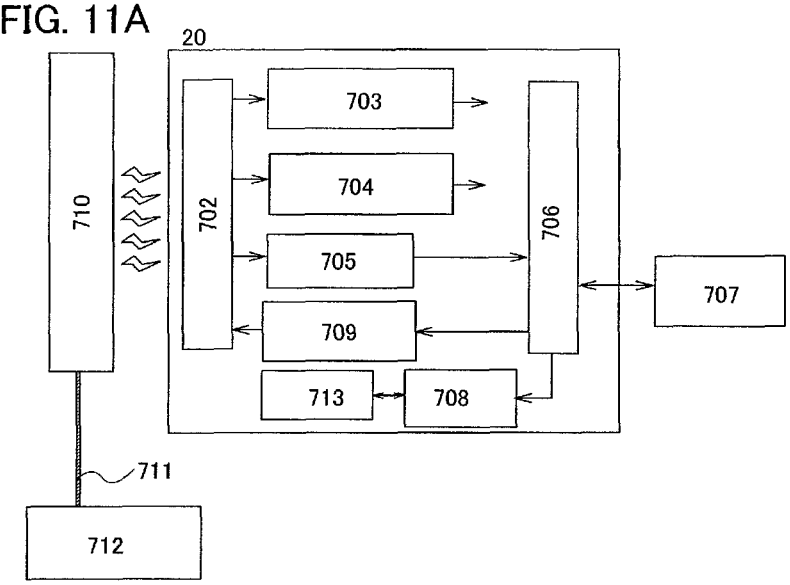
FIGS. 11A and 11B are figures illustrating communication devices of the present invention.

As shown in FIG. 11A, in the case of supplying power wirelessly, the intake unit 20 includes a resonant circuit 702 having an antenna and a resonant capacitor, a power circuit 703, a clock generation circuit 704, a demodulation circuit 705, a control circuit 706, and a modulation circuit 709. Naturally, the intake unit 20 includes an intake means 708 (for example, a pump or the like) and a power supply 713 for intake. Further, the intake unit 20 is provided with an external sensor circuit 707. The sensor circuit 707 is provided on the detection unit 10.

The resonant circuit 702 receives an electric wave transmitted by an antenna 710, and generates an AC signal at both ends of the antenna. The generation AC signal includes information such as instructions transmitted by the antenna 710, and the AC signal may supply power of the sensor circuit 707 or supply power of the intake unit 20 in addition. In the power circuit 703, the AC signal generated in the resonant circuit 702 is rectified using a diode, and smoothed using a capacitor, thereby generating power supply voltage and supplying it to each circuit. The clock generation circuit 704 generates clock signals having various frequencies based on the AC signal generated in the resonant circuit 702. The demodulation circuit 705 demodulates information included in the AC signal generated in the resonant circuit 702. The control circuit 706 extracts an instruction from the demodulated signal, and executes a series of operations in accordance with the instruction by controlling the sensor circuit 707. In addition, a circuit for checking whether the demodulated signal has an error or not may be provided. Next, a writing instruction is sent to the sensor circuit 707, and information stored in a register or the like is stored in a predetermined memory region of the sensor circuit 707. Naturally, the information may be directly stored without being stored in the register. The control circuit 706 can send reading instruction to the sensor circuit 707 to read information. Then, a signal encoded by an encoding circuit in the control circuit 706 is generated and output to the modulation circuit 709. The modulation circuit 709 has a function of modulating a carrier wave based on the encoded signal.

The sensor circuit 707 may preferably be provided with a memory. By using the memory, the number of detected detection objects can be recorded, or positional information of measurement can be stored. Naturally, the memory may be provided on the intake unit. The memory can be formed from one or more selected from a DRAM (Dynamic Random Access Memory), an SRAM (Static Random Access Memory), an FeRAM (Ferroelectric Random Access Memory), a mask ROM (Read Only Memory), a PROM (Programmable Read Only Memory), an EPROM (Electrically Programmable Read Only Memory), an EEPROM (Electrically Erasable Programmable Read Only Memory), and/or a flash memory.

The antenna 710 which is capable of wireless communication with the resonant circuit 702 is connected to an information processing device 712 through a communication line 711, and transmission and reception of information can be carried out between the antenna and the intake unit 20 under control of the information processing device 712. As such an antenna 710, a base station connected to the public telephones can be applied. The antenna 710 and the information processing device 712 may transmit and receive information by wireless communication such as infrared communication. Such an information processing device 712 may be mounted on a public telephone.

In the case where the intake means 708 cannot be operated with power supplied from the power circuit 703, it can be operated with power supplied from the power supply 713 for intake. A battery provided in the intake unit can be used as the power supply 713 for intake.

In the case of connecting a detection unit having the sensor circuit 707 to the intake unit 20 as shown in FIG. 11A, the detection unit, at least the detector, can be replaced.

Figure 11B:
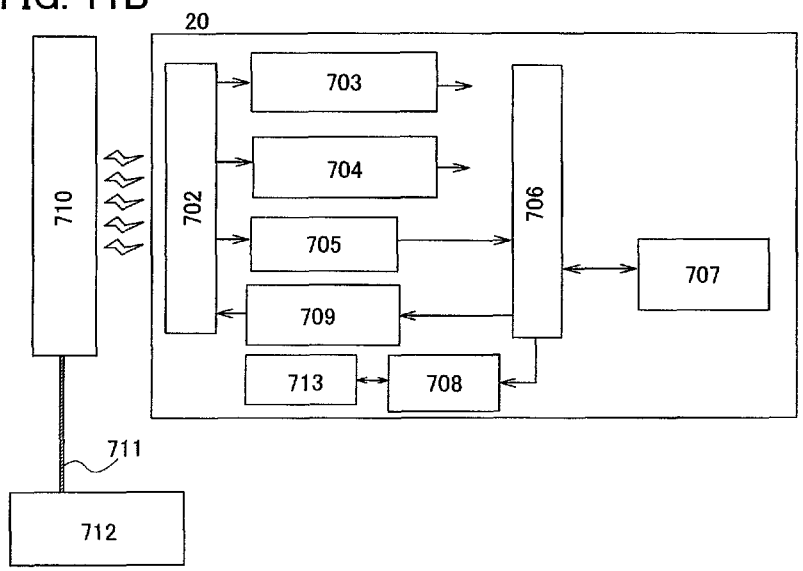

As shown in FIG. 11B, the intake unit 20 may include the sensor circuit 707. When the intake unit 20 is integrated with the sensor circuit 707, the particle detection sensor can be downsized.

The intake unit 20 is not limited to the above structure, and it may have a central processing unit (CPU), a congestion control circuit, or the like. Further, in this embodiment mode, power is supplied from the antenna 710 to the intake unit 20;

however, the present invention is not limited thereto. For example, the intake unit 20 may only transmit and receive information to/from the antenna 710 wirelessly, and may obtain power from only the battery inside.

In such a manner, detection object information or power can be supplied by wireless communication. Note that in this embodiment mode, the intake unit 20 has a function of wireless communication; alternatively, the detection unit may have the wireless communication function.

In this embodiment mode, the intake unit performs wireless communication; however, the intake unit may perform wire communication. When wire communication is carried out, much information can be transmitted and received in a short time, and power can be obtained from a fixed power supply.

This embodiment mode can be freely combined with the above embodiment mode.

Embodiment Mode 3

In this embodiment mode, a detector of a detection unit and its behavior will be explained.

Figure 2:
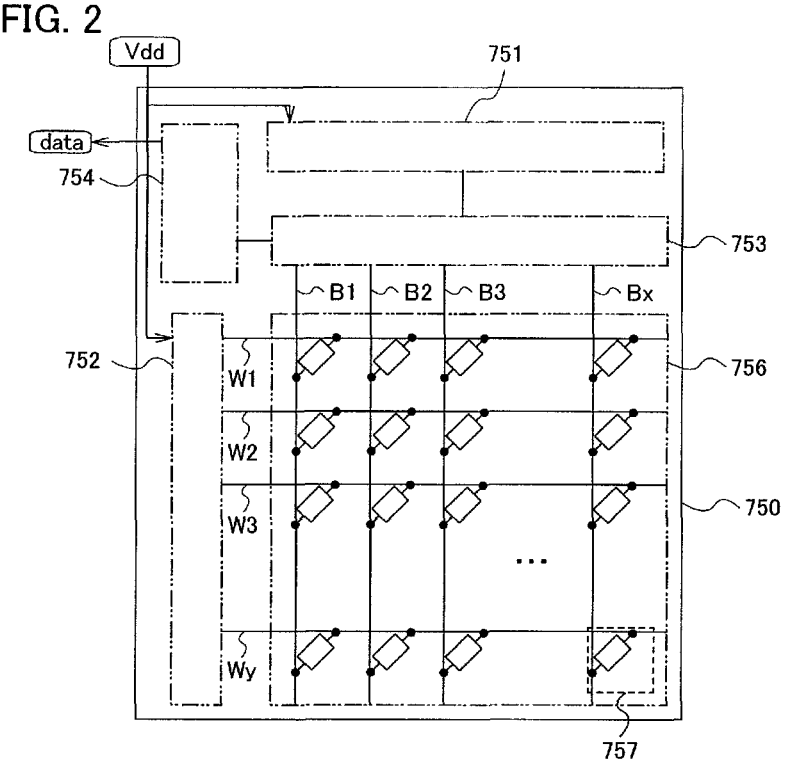
FIG. 2 is a figure illustrating a configuration of a detection unit of the present invention.

As shown in FIG. 2, a detector 750 has a cell array 756 in which detecting elements are formed and a driver circuit. The driver circuit includes a column driver 751, a row driver 752, a selector 753, and a read circuit 754.

The column driver 751 has a function of supplying a signal to the selector 753 in response to an address signal which addresses an arbitrary bit line. The selector 753 has a function of selecting the addressed bit line in response to the signal of the column driver 751. The row driver 752 has a function of selecting an addressed word line in response to the address signal which addresses an arbitrary word line. Through the above operations, one detecting element 757 corresponding to the address signal is selected among the detecting elements. Further, the read circuit 754 reads information in the selected detecting element and outputs it.

The cell array 756 has bit lines Bm (m=1 to x), word lines Wn (n=1 to y), and a detecting element 757 at each point of intersection of the bit lines and the word lines. Further, the bit lines Bm are controlled by the selector 753, and the word lines Wn are controlled by the row driver 752. Note that the detecting element 757 may be an active type to which a transistor is connected, or a passive type which is formed only from the element.

Next, the structure of the detecting element 757 will be explained. The detecting element 757 has a switching device (referred to as a MEMS switch) having a MEMS structure. The MEMS switch has a pair of electrodes having a bridge structure in which the pair of electrodes are partially in contact, and a detection object can be detected when the pair of electrodes detach from each other by adsorption of the detection object. Note that a bridge structure means, for example, in a structure formed over a substrate, either end is fixed and the center does not contact the substrate, or the structure partially fixed to the substrate and the other part does not contact the substrate. The structure or the manufacturing method of the MEMS switch will be described in the following embodiment mode.

The detecting element 757 shown in FIG. 2 is an active type element having a transistor and a MEMS switch. A thin film transistor (also referred to as a TFT) formed from a thin film material or a MOS transistor formed from a silicon wafer can be applied to the transistor. Note that, in the case of using a TFT formed from a thin film material, the detector can be made to be thinner and lighter. In addition, since a TFT can be formed over an insulating substrate such as a glass substrate, the detector can be provided at low price.

A gate electrode included in the transistor is connected to a word line Wy, and either one of a source electrode or a drain electrode included in the transistor is connected to a bit line Bx, and the other is connected to the MEMS switch. A lower electrode of the MEMS switch is electrically connected to the one of the source electrode and the drain electrode included in the transistor. An upper electrode of the MEMS switch can be shared as a common electrode by each detecting element.

Figure 5:
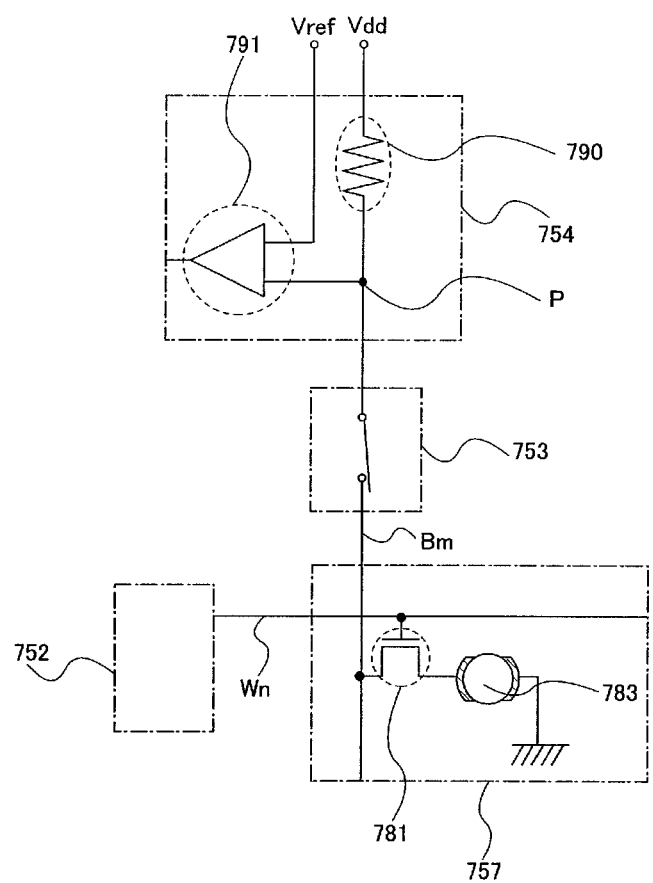
FIG. 5 is a figure illustrating operation of a detection unit of the present invention.

Next, operation of reading information of the active type detecting element 757 will be described with reference to FIG. 5. Note that in this embodiment mode, the detecting element shall store a value "0" in an initial state where the MEMS switch is conducting without separation, and the detecting element shall store a value "1" in a state where the MEMS switch is non-conducting due to adsorption of a detection object or the like.

The resistance value of the initial state is low, and the resistance value of the detecting element after a change becomes high. Such variance of a resistance value is read by the read circuit 754. In order to determine the variance of a resistance value, the read circuit 754 includes a resistor 790 and a sense amplifier 791. Information is read as follows: voltage is applied between the pair of electrodes forming the MEMS switch, and whether the detecting element 757 is in an initial state where the resistance value is relatively low, or in a state after a change where the resistance value is relatively high is determined. Thus, information can be read by resistance division.

For example, the case of reading information on whether the detection object is captured in the MEMS switch 783 in the m-th column of the n-th row or not will be described. First, the bit line Bm of the m-th column and the word line Wn of the n-th row are selected by the column driver 751, the row driver 752, and the selector 753. Then, the transistor 781 included in the detecting element 757 arranged in the m-th column of the n-th row is turned on; therefore, the MEMS switch 783 and the resistor 790 are connected in series. The potential of one end of the resistor 790 shall be Vdd. As to such a detecting element, the potential at a point P shown in FIG. 5 is determined in accordance with the current characteristics of the MEMS switch 783.

Assuming that the potential at the point P is V1 in the case where the detecting element is in the initial state, and the potential at the point P is V2 in the case where the detecting element is separated after change; by using a reference potential Vref which satisfies V2>Vref>V1, information on whether a detection object is adsorbed to the detection element or not can be read. Specifically, when the detecting element is in the initial state, the output potential of the sense amplifier 791 is High. Meanwhile, when the detecting element is in state after change, the output potential of the sense amplifier 791 is Low.

In accordance with the aforementioned method, the read circuit 754 reads the information in the MEMS switch 783 with a voltage value using resistance division and a difference between resistance values of the MEMS switch 783. Alternatively, the information in the MEMS switch 783 may be read with a current value. Note that the read circuit 754 of the present invention is not limited to the aforementioned configuration. Any configuration may be used for the read circuit 754 as long as the data in the detecting element can be read.

The MEMS switch 783 having such a configuration changes from a "0" state to a "1" state. Further, the change from a logical value "0" to a logical value "1" is irreversible. Alternatively, when a material which is sufficiently elastic is used as the material of electrodes of the MEMS switch, a structure in which electrodes which are separated once are in contact when the electrodes are unloaded can be used.

In a cell array in this embodiment mode, particles which are smaller than holes for the detection fall through the holes. Accordingly, untargeted small particles are not detected when passing through the holes.

Further in the cell array, when detecting elements including detection holes each having a different diameter are formed over one substrate, the sizes and the number of the captured detection objects can be detected according to the coordinates of transistors. Thus, even in the case where pollen is a detection object, pollen grains having different sizes depending on the kinds of plants and growing conditions can be detected.

The shape of the detection holes is not limited to a circular shape, and the detection holes may have a rectangular shape or an elliptical shape.

Using a detection manner of the invention, any particle having a spherical shape with similar diameters can be detected.

Note that this embodiment mode can be implemented in any combination with the above embodiment modes.

Embodiment Mode 4

In this embodiment mode, the concept of a MEMS switch provided on a detection unit will be described.

Figure 3:
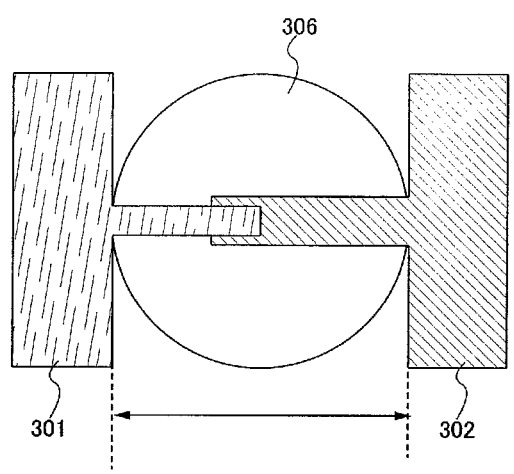
FIG. 3 is a figure illustrating a structure of a switch of the present invention.

A MEMS switch may be formed using electrodes 301 and 302 having a bridge structure in which the electrodes are partially in contact (See FIG. 3). A detection hole 306 to which a detection object can be adsorbed is provided between the electrodes 301 and 302. In other words, the electrodes 301 and 302 are provided over a path of an air current flowing into the detection hole 306.

Then, a detection object is adsorbed to a detection hole of the MEMS switch. For example, pressure of the atmosphere where the MEMS switch is provided is reduced, and thus the detection object is adsorbed to the detection hole. Such a detection object brings the MEMS switch to an ON-state (contact state) or an OFF-state (non-contact state). An ON-state means a state where the electrodes 301 and 302 are in contact and current flows while a detection object is not in contact with the electrodes 301 and 302. Meanwhile, an OFF-state means a state where the electrodes 301 and 302 are detached by a detection object, and current does not flow. Thus, when a detection object is adsorbed to the detection hole, the electrodes 301 and 302 are detached, and an OFF-state is established.

FIG. 3 shows a top view of a MEMS switch, and FIGS. 4A to 4C respectively show a cross-sectional view of a MEMS switch, a cross-sectional view of a MEMS switch in an ON-state, and a cross-sectional view of a MEMS switch in an OFF-state. The electrodes 301 and 302 are formed in detection holes, namely on a base 300 provided with an opening. The ends of the base 300 at the detection hole may preferably be tapered. Thus, detection objects can be quickly captured. In the case where the ends of the base have a tapered shape, the diameter of the detection hole 306 has a first diameter (t4) between end portions of the base with smaller angles, and a second diameter (t5) which is longer than the first diameter between end portions of the base with larger angles. The first diameter (t4) is preferably rather smaller than the diameter of a detection object. Preferably, the first diameter (t4) is approximately 60% to 90% of the diameter of a detection object. Here, when the first diameter (t4) is determined so as to be almost the same width of the detection object at the position which is 20% to 30% of the diameter from the bottom point of contact of the detection object, which is about 60% to 90% of the diameter. When detection holes have a diameter of approximately 60% to 90% of the diameter of detection objects, the electrodes 301 and 302 can be detached efficiently due to the adsorption of the detection objects.

The taper angle of the base 300 at the detection hole can be determined corresponding to the second diameter (t5). The tapered corner is preferably rounded.

A length (t1) of the electrode 301, a length (t2) of the electrode 302, and a length (t3) of a part where the electrodes overlap can be determined corresponding to the diameter of the detection hole 306. When the overlap length (t3) is longer, the contact area of the electrode 301 and the electrode 302 is larger, so that the resistance value can be lowered. The length (t1) of the electrode 301 and the length (t2) of the electrode 302 are preferably about a half of the diameter of the detection hole 306. That is because the overlapping region of the electrodes 301 and 302 can be set at the center of the detection hole 306.

In this state, pressure in the atmosphere under which the MEMS switch is provided can be reduced by an intake unit. Consequently, accuracy of the adsorption of detection objects can be improved.

FIG. 4B shows a cross-sectional view of a state immediately before the detection object 305 contacts the electrodes 301 and 302. The electrodes 301 and 302 are in contact with each other, which allows current to flow, and the resistance is reduced. Such a state is called an ON-state.

FIG. 4C shows a cross-sectional view of a state where the detection object 305 is in contact with the electrodes 301 and 302. When the detection object 305 is in contact with the electrodes 301 and 302, the electrodes 301 and 302 are separated, so that current does not flow, and the resistance is increased. Such a state is called an OFF-state.

Since the MEMS switch is provided in a reduced pressure atmosphere, the detection object 305 is actively adsorbed to the detection hole 306. When the size of the detection hole 306, namely, distance between the electrodes 301 and 302 is determined, the size of detection objects to be detected can be determined. When detection holes having different sizes are provided over one substrate, detection objects having different sizes can be detected.

Since pollen is positively charged in general, it is preferable that a negative current flows in the electrodes 301 and 302.

The structure of a MEMS switch described in this embodiment mode is only an example, and any structure can be used as long as the pair of electrodes are in contact before a detection object is adsorbed to a detection hole, and the pair of electrodes are separated by adsorption of a detection object, without limitation to the structure shown in FIGS. 4A to 4C. A structure of a MEMS switch may also have at least one conductor which is capable of transforming and a base with an opening, the one conductor being under the base and the opening.

Further, detection objects are detected when the MEMS switch changes from the ON-state to the OFF-state in the above explanation; however, detection objects may be detected when the MEMS switch changes from the OFF-state to the ON-state.

Figure 16A:
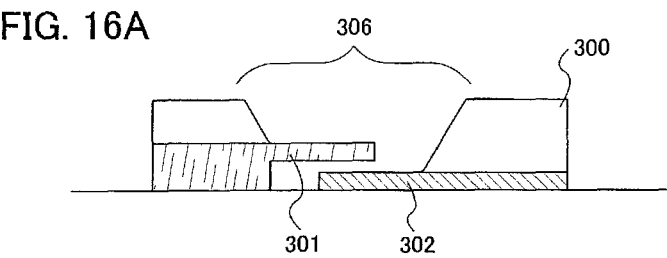
FIGS. 16A to 16C are figures illustrating operation of a switch of the present invention.

For example, as shown in FIG. 16A, a MEMS switch in an OFF-state in which electrodes 301 and 302 are not in contact is prepared. A detection hole 306 is a hole which can catch a detection object. In the case of detecting detection objects having the same size, the base 300 is processed so as to have a larger depth and a shorter diameter as compared with FIGS. 4A to 4C.

Figure 16B:
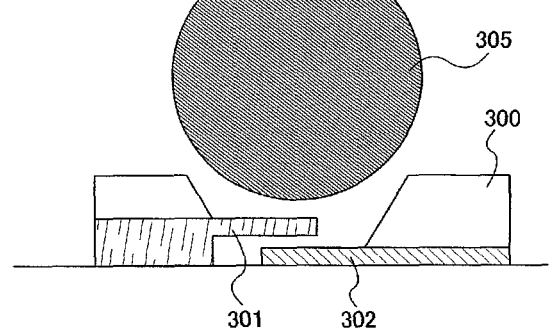

FIG. 16B shows a cross-sectional view of a state immediately before a detection object 305 contacts the electrodes 301 and 302. The electrodes 301 and 302 are not in contact with each other, namely in an OFF-state where current does not flow.

Figure 16C:
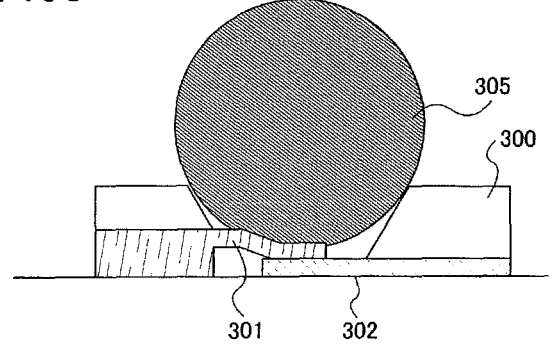

FIG. 16C shows a cross-sectional view of a state where the detection object 305 contacts the electrodes 301 and 302. When the detection object 305 is in contact with the electrodes 301 and 302, the electrodes 301 and 302 are in contact with each other, which is an ON-state where current flows. Since resistance is higher in the ON-state as compared with an OFF-state, the number of detection objects can be counted by reading it.

Note that this embodiment mode can be implemented in any combination with the above embodiment modes.

Embodiment Mode 5

In this embodiment mode, use of a particle detection sensor of the invention for detecting pollen will be described.

As shown in FIG. 12, particle detection sensors of the invention are provided in certain areas controlled by base stations. For example, a person having a particle detection sensor A is in an area A controlled by a base station A. Meanwhile, persons having particle detection sensors B and C are respectively in areas B and C respectively controlled by base stations B and C. The number of pollen grains in the areas A to C can be counted with the particle detection sensors A to C.

Further, pollen information of many areas can be accumulated using communication functions of the particle detection sensors A to C. The particle detection sensors can have communication functions by connecting the particle detection sensors to cellular phones. Note that particle detection sensors themselves may have communication functions. Information on the positions and the amount of pollen can be sent to a nearest base station using a particle detection sensor having a communication function. The base station transmits the information to a central management center, thereby collecting information of pollen in many areas.

The central management center regards the collected information as pollen amount, determines whether the pollen amount is more or less as compared with the peripheral regions, and can distribute a result to cellular phones. Further, the collected information on the pollen amount can be provided for many people including measurers, using display devices or the like. For example, a pollen map showing whether the amount of pollen is large or small per each region is made based on the collected information of the pollen amount. The pollen map can be distributed to cellular phones or displayed on a display device.

In addition, if measurers input information on the climate or whether the measurement area is in doors or out of doors, more accurate information can be obtained.

In the case where a detection unit of the invention wirelessly transmits/receives signals to/from a base station, when the detection unit receives an electric wave transmitted by an antenna 710 with a resonant circuit 702, a power supply electric potential is generated by the power circuit 703. Further, information is demodulated from the electric wave received with the demodulation circuit 705. The information is transmitted by the modulation circuit 709. In this manner, the detection unit can transmit and receive information to/from the base station through wireless communication.

Next, the configuration of a particle detection sensor, a base station, a central management center, and a display device will be described.

Figure 13:
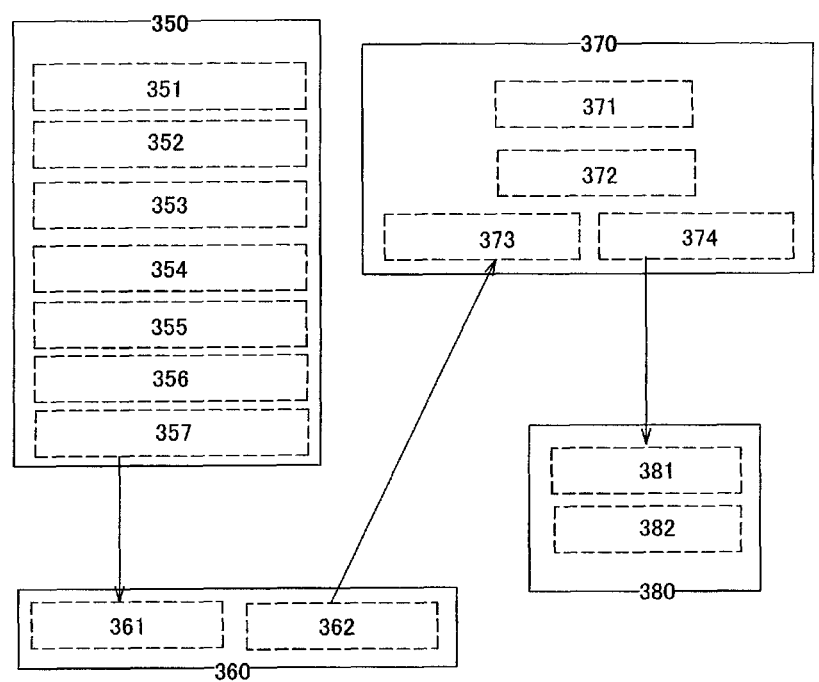
FIG. 13 is a figure illustrating operation of a detection unit of the invention.

As shown in FIG. 13, a particle detection sensor 350 has a detector 351. The detector 351 is provided with a MEMS switch and a driver circuit described in the above embodiment mode. The particle detection sensor 350 includes a display area 352 for displaying detection results and an input unit 353 for inputting information. Positional information can be inputted to the input unit 353. The positional information includes a present location or a destination. In addition, a positional information control device 354 which is a system for managing positional information, such as a GPS may be provided. Using the positional information control device 354, positional information of measurers can be automatically obtained, and the measurers need not input the positional information. The particle detection sensor 350 has a memory device 355 for storing the obtained information. The particle detection sensor 350 has a computing device 356 which calculates the detection number based on the detection result. The computing device 356 can associate the total of the detection number and the detection area which are obtained from a driver circuit of the detector 351. Further, the particle detection sensor 350 can communicate with a base station 360 by being provided with a communication device 357. Wire communication or wireless communication can be applied to the communication. Wire communication can be conducted by connecting a telephone station of a public telephone or the like and a communication device. Thus, wire communication has limitation on the area of information transmission. Note that in the case of wire communication, the amount of information transmitted is more than the case of wireless communication, and the transmission can be performed in a short time, which is advantageous.

The display area 352, the input unit 353, the positional information control device 354, the memory device 355, the computing device 356, or the communication device 357 can be externally provided on the particle detection sensor 350 or provided on an intake unit. For example, by connecting a cellular phone to the particle detection sensor 350, the particle detection sensor 350 can be equipped with at least the display area 352, the input unit 353, the positional information control device 354, the computing device 356, and the communication device 357.

The base station 360 includes a first communication device 361 for transmitting/receiving information to/from the particle detection sensor 350. The base station 360 includes a second communication device 362 for transmitting/receiving information to/from a central management center 370. One communication device can serve as both the first communication device 361 and the second communication device 362; however, they are preferably provided separately for obtaining new information continuously from the particle detection sensor 350, and transmitting the information sequentially to the central management center 370. The first communication device 361 preferably performs wireless communication, and the second communication device 362 may perform wire communication. That is because it is difficult to fix the particle detection sensor 350 and the base station, meanwhile, the base station 360 and the central management center 370 are often fixed.

The central management center 370 has an arithmetic processing unit 371, a memory device 372, a first communication device 373, and a second communication device 374. Using the arithmetic processing unit 371, the accumulated pollen information or the like can be analyzed, and a pollen map can be formed. The memory device 372 can store the accumulated pollen information and the analyzed information of pollen or the like. The first communication device 373 enables communication with the base station 360, and the second communication device 374 enables communication with a display device 380. Since the display device 380 is often fixed as well, the second communication device 374 may perform wire communication.

The display device 380 includes a driver circuit area 381, and a display area 382. The display area 382 can display the analyzed information of pollen or the like. The driver circuit area 381 has a function of converting information obtained from the central management center 370 into video information through the second communication device 374 and controlling display based on the video information.

Using the particle detection sensor 350, the base station 360, the central management center 370, and the display device 380, pollen information can be provided for many people including measurers.

Figure 14A:
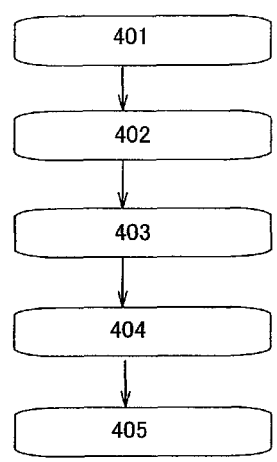
FIGS. 14A to 14C are flowcharts of operations of a detection unit of the present invention.
Figure 14B:
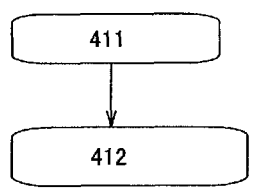
Figure 14C:
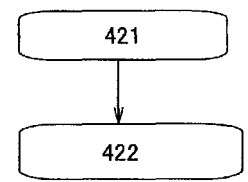

FIGS. 14A to 14C show flowcharts of providing pollen information. As shown in FIG. 14A, pollen detection is conducted in a certain area using a particle detection sensor (401). Then, the detection result is obtained using an arithmetic circuit provided on the particle detection sensor (402). The detection result is transmitted to a base station through a communication device, and then transmitted to a central management center (403). The central management center can conduct analysis and summation based on the transmitted detection result (404). Here, much pollen information is collected, and pollen information associated with the position can be formed. The result is provided as pollen information (405). For example, a pollen map on which the amounts of pollen are inscribed can be given as one of pollen information.

FIG. 14B shows another mode. First, a destination is transmitted to a central management center (411). Then, pollen information of that area can be obtained (412). Specifically, pollen information of the destination based on accumulated pollen information or a pollen map formed is provided by the central management center.

Alternatively, as shown in FIG. 14C, pollen information can be obtained (422) by directly accessing a server recording pollen information or the like obtained by the central management center (421).

Thus, pollen information of each place can be collected using a particle detection sensor equipped with a MEMS switch, and the information can be provided for a great number of people. Consequently, the accuracy of the pollen information can be increased, and pollen information of a destination other than that of the present location can be obtained.

In this embodiment mode, the case of transmitting the detection result to the central management center through the base station is described; alternatively, the detection result can be directly transmitted to the central management center.

In this embodiment mode, the case of using a particle detection sensor carried by people is described; however, pollen information can also be collected using particle detection sensors fixed at certain intervals.

Note that this embodiment mode can be implemented in any combination with the above embodiment modes.

Embodiment Mode 6

A particle detection sensor of the invention can be manufactured through a semiconductor element manufacturing process using a silicon wafer; however, such a manufacturing process has an issue of cost reduction in order to achieve mass production. Accordingly, this embodiment mode will describe a process in which a microstructure of the invention is formed using a thin film material over an insulating substrate which can be formed at lower cost compared with a silicon wafer, and further integrated with a semiconductor element. Note that in this embodiment mode, a thin film transistor is used as the semiconductor element.

Figure 6A:
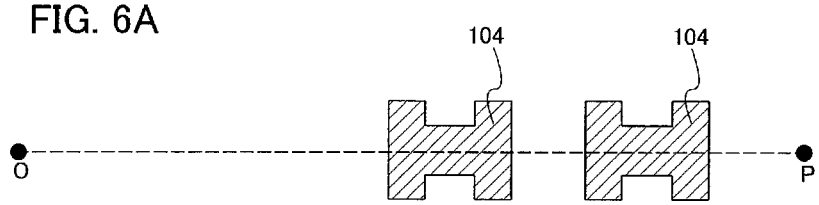
FIGS. 6A and 6B are figures illustrating a manufacturing step of a detection unit of the present invention.
Figure 6B:
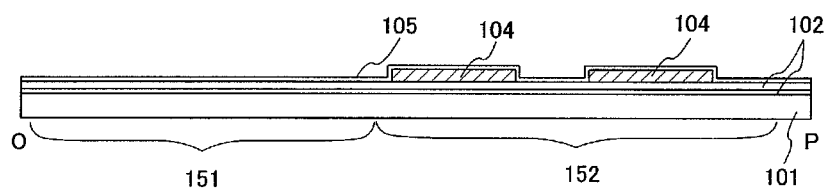

FIG. 6A shows a top view while FIG. 6B shows a cross sectional view taken along line O-P. First, an insulating substrate 101 is prepared. The insulating substrate 101 may be a glass substrate, a quartz substrate, a plastic substrate, or the like. Moreover, it is possible to use a conductive substrate such as a metal or a semiconductor substrate such as a silicon substrate over which an insulating layer is formed. By forming a microstructure over a plastic substrate, a particle detection sensor which is highly flexible and thin can be formed. Further, by forming a glass substrate which is made thinner by polishing or the like, a particle detection sensor can also be formed.

A base layer 102 is formed over the insulating substrate 101 by CVD or sputtering (see FIG. 6B). The base layer 102 can be formed of a single layer or a layered structure using an oxide of silicon such as silicon oxide, a nitride of silicon such as silicon nitride or silicon oxynitride. In this embodiment mode, two-layer structure is employed for the base layer 102. As a first layer of the base layer 102, a silicon oxynitride layer can be formed to a thickness of 10 nm to 200 nm (preferably 50 nm to 100 nm) by plasma CVD using $SiH_4$, $NH_3$, $N_2O$, and $H_2$ as a reactive gas. In this embodiment mode, a silicon oxynitride layer is formed to a thickness of 50 nm. Subsequently, as a second layer of the base layer 102, a silicon oxynitride layer can be formed to a thickness of 50 nm to 200 nm (preferably 100 nm to 150 nm) by plasma CVD using $SiH_4$ and $N_2O$ as a reactive gas. In this embodiment mode, a silicon oxynitride film is formed to a thickness of 100 nm.

Next, a semiconductor layer 104 forming a semiconductor element is formed in a semiconductor element region 152 but not in a microstructure region 151. The semiconductor layer can be formed from a silicon material or a material containing silicon and germanium. The semiconductor layer may be in an amorphous state, a polycrystalline state, or a microcrystalline state. The, the semiconductor layer 104 is processed into an arbitrary shape. In this embodiment mode, the semiconductor layer 104 is processed into a rectangular shape (See FIG. 6A). The semiconductor layer 104 is processed by patterning a resist using photolithography and dry etching.

Next, a gate insulating layer 105 is formed over the semiconductor layer 104 (FIG. 6B). The gate insulating layer 105 can be formed using a material, a structure, and a method which are similar to those used in forming the base film 102. In this embodiment mode, a silicon oxynitride layer with a thickness of 115 nm (composition ratio: Si=32%, O=59%, N=7%, and H=2%) is formed by plasma CVD as the gate insulating layer 105.

As a material of the gate insulating layer 105, an organic material can be used other than an inorganic material. For example, an organic material containing silicon may be used to form the gate insulating layer 105 by spin coating or an application method by coating.

Further, as a material of the gate insulating layer 105, a metal oxide having high dielectric constant, for example, hafnium (Hf) oxide can be used. When the gate insulating layer is formed using such a high dielectric constant material, the semiconductor element can be driven at a low voltage; thus, a low power consumption semiconductor device can be obtained.

The gate insulating layer 105 can be formed by high density plasma treatment. The high density plasma treatment is a plasma treatment in which the plasma density is $1\times10^{11}$ $cm^{-3}$ or more, preferably $1\times10^{11}$ $cm^{-3}$ to $9\times10^{15}$ $cm^{-3}$ and a high frequency such as a microwave (for example, frequency: 2.45 GHz) is used. When plasma is produced under such conditions, the low electron temperature is 0.2 eV to 2 eV, thus generating plasma at a low electron temperature. Thus, by high density plasma, the feature of which is low electron temperature, a film can be formed with low plasma damage and few defects because the kinetic energy of the active species is low.

The insulating substrate on which the semiconductor layer 104 has been formed, that is, a formation object, is set in a film formation chamber capable of such plasma treatment, and distance between an electrode for generating plasma, which is an antenna, and a target is set 20 mm to 80 mm apart, preferably 20 mm to 60 mm apart, then high density plasma treatment is carried out. Such high density plasma treatment can make a low temperature process (substrate temperature: 400° C. or less) possible. Accordingly, glass or plastics having low thermostability can be used as the insulating substrate 101.

The atmosphere in the film formation chamber may be a nitrogen atmosphere, or an oxygen atmosphere. The nitrogen atmosphere is typically a mixed atmosphere of nitrogen and rare gas, or a mixed atmosphere of nitrogen, hydrogen, and rare gas. At least one of helium, neon, argon, krypton, and xenon can be used as the rare gas. Further, the oxygen atmosphere is typically a mixed atmosphere of oxygen and rare gas; a mixed atmosphere of oxygen, hydrogen, and rare gas; or a mixed atmosphere of dinitrogen monoxide and rare gas. At least one of helium, neon, argon, krypton, and xenon can be used as the rare gas.

The insulating layer formed as above is dense and causes little damage to other films. Further, the state of an interface between the insulating layer and a layer to be in contact therewith can be improved. For example, when the gate insulating layer 105 is formed by high density plasma treatment, a state of an interface with the semiconductor layer 104 can be improved. Accordingly, electrical properties of the semiconductor element can be improved.

Here, the case of forming the gate insulating layer 105 using high density plasma treatment is described; however, the base layer 102 or other insulating layers can also be formed by high density plasma treatment. The surface of the semiconductor layer 104 can be improved by the high density plasma treatment. Consequently, the state of an interface can be improved and the electrical properties of the semiconductor element can be improved. Note that in the top view of FIG. 6A, the insulating substrate 101, the base layer 102, and the gate insulating 105 are omitted.

Figure 7A:
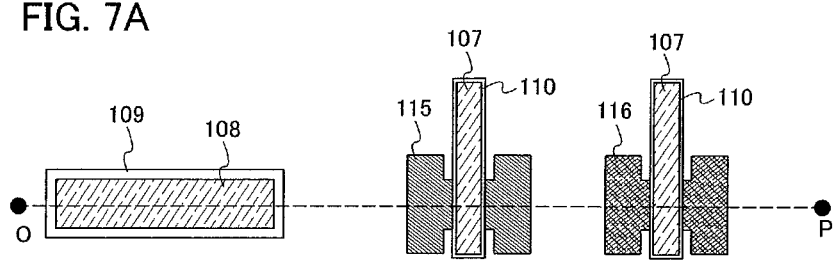
FIGS. 7A and 7B are figures illustrating a manufacturing step of a detection unit of the present invention.
Figure 7B:
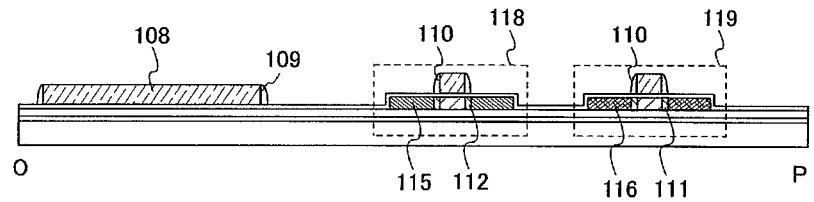

Next, as shown in FIGS. 7A and 7B, a gate electrode 107 and a conductive layer which later becomes a sacrificial layer 108 forming a micro channel for reducing pressure are formed over the gate insulating layer 105. The conductive layer can be formed by sputtering or CVD using a metal such as titanium (Ti), aluminum (Al), molybdenum (Mo), tungsten (W), or tantalum (Ta); or a material containing a nitride of the metal. The conductive layer can have a single layer structure or a layered structure. The conductive layer is processed into a shape by patterning a resist mask using photolithography and dry etching. As an example of etching, ICP (Inductively Coupled Plasma) etching can be used. Hereupon, etching conditions (the amount of power applied to a coil electrode, the amount of power applied to an electrode on the substrate 101 side, the temperature of the electrode on the substrate insulating 101 side, and the like) are adjusted as appropriate. As an etching gas, a chlorine-based gas typified by $Cl_2$, $BCl_3$, $SiCl_4$, $CCl_4$, or the like; a fluorine-based gas typified by $CF_4$, $SF_6$, $NF_3$, or the like; or $O_2$ can be used as appropriate. The processed conductive layer is to be a gate electrode 107 or a sacrificial layer 108.

Further, when the gate electrode 107 is formed, the end portion of the gate electrode 107 may preferably tapered. For example, a gate electrode having a layered structure can be tapered by anisotropic etching using the difference in the etching rate.

Hereupon, the thickness of the sacrificial layer 108 is desirably 1 μm or more and 3 μm or less in consideration of forming the micro channel for reducing pressure after etching the sacrificial layer 108 away; meanwhile, the gate electrode does not require such thickness in view of microfabrication. Then, a part to be the gate electrode 107 can be made thin by using a mask which is formed with an exposure mask provided with a resist mask formed with an auxiliary pattern having a diffraction grating pattern or a semi-transmissive film having a function of reducing the intensity. For example, the thickness of the gate electrode 107 can be made to be approximately half of the thickness of the sacrificial layer 108. In the case of using an exposure mask having a function of reducing light intensity, light transmittance of the region can be controlled to be in the range of 10% to 70%. When the resist mask is exposed using such an exposure mask, resist masks having different film thicknesses can be formed. By processing the conductive layer using resist masks having different film thicknesses, the film thickness of the gate electrode 107 and the thickness of the sacrificial layer 108 can be made different.

Further, the sacrificial layer 108 may have a desired thickness by repeating deposition and processing, to have a different thickness from the gate electrode. In the case of repeating film formation or processing, the stress of the sacrificial layer due to film formation can be reduced.

Next, a semiconductor layer 104 forming a semiconductor element is added with an impurity element to form an n-type impurity region 112 and a p-type impurity region 111. The impurity element is added by ion doping or ion implantation. As an impurity element which imparts n-type conductivity, phosphorus (P) or arsenic (As) is typically used, and as an impurity element which imparts p-type conductivity, boron (B) can be used. It is desirable that the n-type impurity region 112 and the p-type impurity region 111 are added with an impurity element at a concentration range of $1 \times 10^{20}/cm^3$ to $1 \times 10^{21}/cm^3$. Such impurity regions having different polarities can be selectively formed by forming a resist mask by photolithography and adding impurity elements.

Subsequently, an insulating layer of a silicon oxide or a silicon nitride is formed by CVD, and the insulating layer is anisotropically etched in a vertical direction, thereby forming an insulating layer 110 (hereinafter referred to as a sidewall 110) in contact with a side face of the gate electrode 107 (FIG. 7A). Short channel effects caused by decrease in the gate length can be prevented by using the sidewall 110.

At this time, a sidewall 109 in contact with a side face of the sacrificial layer 108 is formed. In the case where a sidewall in contact with a side face of the sacrificial layer 108 is not formed, the sacrificial layer 108 is covered with a mask. Further, when covering with the mask is carried out in a state where an insulator for a sidewall is formed in a region where the sacrificial layer 108 is to be formed, the mask can be used as a protective film over the sacrificial layer 108.

Next, the semiconductor layer 104 having the n-type impurity region 112 is added with an impurity element so as to form a high concentration n-type impurity region 115 having a higher impurity concentration than the n-type impurity region 112 provided under the sidewall 110. In a similar manner, a high concentration p-type impurity region 116 having an impurity concentration higher than that of the p-type impurity region 111 provided under the sidewall 110 can be formed. Since a short channel effect hardly occurs in a p-type semiconductor element compared to an n-type semiconductor element, there is a case where the p-type impurity region 111 is not formed.

Further, in the case where the gate electrode 107 has a tapered shape side, the sidewall 110 is not necessarily formed. In this case, the n-type impurity region 112 and the high concentration n-type impurity region 115 can be formed at one time when an impurity element is added. In a similar manner, the p-type impurity region 111 and the high concentration p-type impurity region 116 can be formed by one time addition of an impurity element.

After the impurity region is formed, heat treatment is preferably carried out to activate the impurity element. A heating furnace, infrared light irradiation, or laser irradiation is used for the heat treatment. Furthermore, at the same time as the activation, plasma damage to the gate insulating layer 105 or the interface between the gate insulating layer 105 and the semiconductor layer 104 can be repaired. Effective activation can be carried out particularly when the impurity element is activated using an excimer laser from the surface or from the back in an atmosphere under room temperature to 300° C. Further, a second harmonic of YAG laser may be used for the activation. The irradiation using the YAG laser is a preferable activation means because the YAG laser requires less maintenance.

Alternatively, after an insulating layer formed of silicon oxide or silicon nitride is formed so as to cover the conductive layer or the semiconductor layer 104, heat treatment, infrared light irradiation, or laser irradiation may be performed. Hydrogen in a silicon oxide or a silicon nitride can be released by heat treatment, infrared light irradiation, or laser irradiation. For example, a silicon oxynitride layer is formed to a thickness of 100 nm by CVD, and then heated using a clean oven at 300° C. to 550° C. for 1 to 12 hours; thus, hydrogen in a silicon oxynitride layer is released, thereby terminating dangling bonds in the semiconductor layer.

Through the above steps, an n-type semiconductor element 118 and a p-type semiconductor element 119 can be formed (FIG. 7B). Note that, in a top view of FIG. 7A, the insulating substrate 101, the base layer 102, and the gate insulating layer 105 are omitted.

Figure 8A:
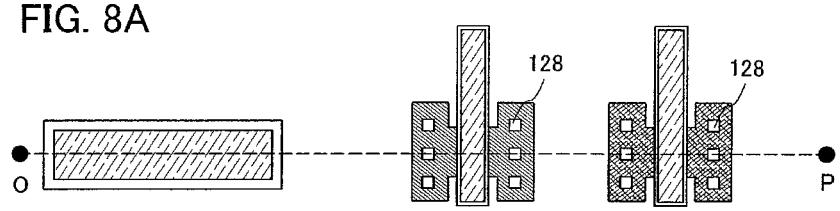
FIGS. 8A and 8B are figures illustrating a manufacturing step of a detection unit of the present invention.
Figure 8B:
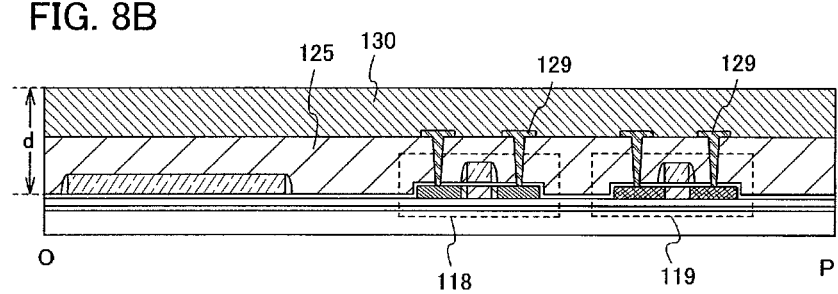

Subsequently, an insulating layer 125 is formed as shown in FIG. 8B. The insulating layer 125 can be formed of an inorganic material or an organic material, or the like, which has insulating properties. Silicon oxide or silicon nitride can be used for the inorganic material. Polyimide, acrylic, polyamide, polyimide amide, a resist, benzocyclobutene, siloxane, or polysilazane can be used as the organic material. The skeletal structure of siloxane is formed from a bond of silicon (Si) and oxygen (O), and an organic group (for example, an alkyl group or aromatic hydrocarbon) containing at least hydrogen is used as the substituent. A fluoro group may also be used as the substituent. Alternatively, an organic group at least containing hydrogen and a fluoro group may be used as the substituent. Polysilazane is formed using a polymer material having a bond of silicon (Si) and nitrogen (N) as a starting material.

Next, the insulating layer 125 and the gate insulating layer 105 are sequentially etched to form a first contact hole 128 (FIG. 8A). Either dry etching or wet etching can be used for forming the first contact hole 128. Note that the insulating layer 125 is omitted in a top view of FIG. 8A and the part of the contact hole 128 to be formed in the insulating layer 125 is schematically shown.

Next, a conductive layer 129 is formed on the insulating layer 125 and in the first contact hole 128, and processed into an arbitrary shape, thereby forming wirings forming a source electrode, a drain electrode, and an electric circuit (FIG. 8B). A film formed of an element such as aluminum (Al), titanium (Ti), molybdenum (Mo), tungsten (W), and silicon (Si), or an alloy film containing any of the above-mentioned elements, can be used for the conductive layer 129. The conductive layer 129 can be processed, for example, by a combination of resist patterning using photolithography and dry etching.

Further, when the conductive layer 129 has a corner when viewed from above, the corners is preferably processed so as to be rounded. Thus, dust generation is suppressed, and yield can be improved. This also applies to the case of processing a conductive layer such as the gate electrode 107.

Next, an insulating layer 130 is formed (See FIG. 8B). The insulating layer 130 can be formed by an insulating inorganic material, an insulating organic material, or the like. The material of the insulating layer 130 or the manufacturing method is similar to those of the insulating layer 125. Accordingly, the same material as the insulating layer 125 can be used for the insulating layer 130, and a different material can also be used instead.

The insulating layers 125 and 130 are preferably formed of an organic material in the case of increasing the planarity. Further, in order to prevent entry of impurity or the like, an inorganic material is preferably used to form them. Therefore, when the insulating layer 125 is formed of an inorganic material and the insulating layer 130 is formed of an organic material, the impurity can be prevented from entering due to the insulating layer 125, and planarity can be increased due to the insulating layer 130, which is preferable.

In order to increase planarity of the insulating layers 125 and 130, the surface can be polished by a CMP (Chemical-Mechanical Polishing) method.

The total film thicknesses (d) of the insulating layer 125 and the insulating layer 130 is desirably 10 μm to 30 μm. Considering the mechanism where a detection object is adsorbed to detection holes later to be formed in the insulating layers 125 and 130, it can be considered that with such film thickness, an air pathway (a detection hole and a micro channel for reducing pressure which are to be formed later) for reducing pressure is not filled, and load of an intake unit when reducing pressure can be reduced. When a detection object fills the channel, the channel becomes narrower, and load on an intake unit is increased. Correspondingly, the film thickness of the insulating layers 125 and 130 in which detection holes are formed is preferably 10 μm to 30 μm which is a length equal to or more than the radius of a detection object. Note that in a top view of FIG. 8A, the insulating substrate 101, the base layer 102, the gate insulating layer 105, the insulating layer 125, the conductive layer 129, and the insulating layer 130 are omitted.

Figure 9A:
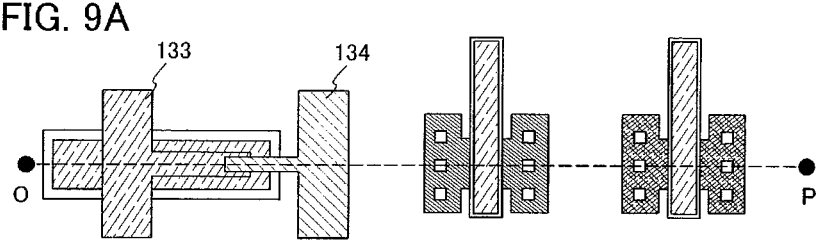
FIGS. 9A and 9B are figures illustrating a manufacturing step of a detection unit of the present invention.
Figure 9B:
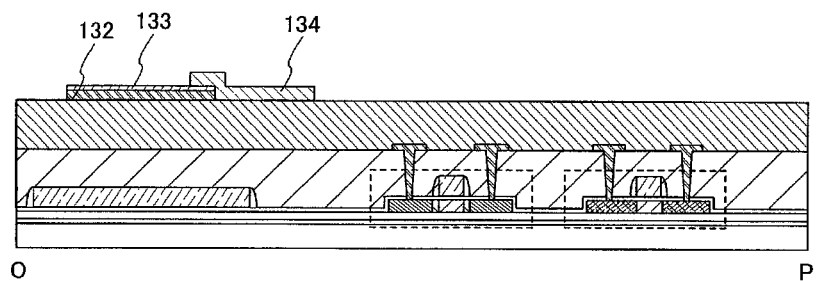

As shown in FIGS. 9A and 9B, a conductive layer is formed over the insulating layer 130, and a first electrode 132 to be a detector is formed by processing the conductive layer. Such a conductive layer can be formed of a metal such as titanium (Ti), aluminum (Al), molybdenum (Mo), tungsten (W), or tantalum (Ta); or a material containing a nitride of such a metal by sputtering or CVD. The conductive layer can have a single layer structure or a layered structure. The conductive layer can be processed by resist patterning using photolithography and dry etching. Here, the shape of the processed first electrode 132 is elongated and provided along the diameter of the detection hole to be later formed in the insulating layers 125 and 130. The first electrode 132 is, for example, processed to have a length half the diameter of the detection hole. The first electrode 132 has a cantilever structure in which space to be a detection hole is provided therebelow; therefore, in the case of lacking strength, reinforcement may be provided. For example, silicon oxide or silicon nitride is formed under the first electrode 132 for the reinforcement.

Next, a sacrificial layer 133 is formed over the first electrode 132, and processed to have a predetermined shape. The sacrificial layer 133 can be processed by resist patterning using photolithography and dry etching. The sacrificial layer 133 can be formed from a material containing metals such as titanium (Ti), aluminum (Al), molybdenum (Mo), or tungsten (W), or also can be formed from a silicon layer, silicon oxide, silicon nitride, or the like. Alternatively, the sacrificial layer 133 can be formed from a metal compound which is a compound of the aforementioned metal and silicon. In addition, the sacrificial layer 133 may be formed to have either a single layer structure or a layered structure. In the case of a layered structure, a material selected from the aforementioned materials may be stacked. The sacrificial layer 133 may be formed of any material which can have etching selectivity to the first electrode 132, meanwhile, processing can be easily done when a material the same as the insulating layer 125 or the insulating layer 130 is used.

Further, the first electrode 132 and the sacrificial layer 133 can be processed in one step. In this case, the shapes of the first electrode 132 and the sacrificial layer 133 often correspond when viewed from above. A top view of FIG. 8A shows the case where the shapes of the first electrode 132 and the sacrificial layer 133 correspond.

Next, a conductive layer is formed over the sacrificial layer 133, and the conductive layer is processed into a predetermined shape to form a second electrode 134. The second electrode 134 uses a cantilever structure in which space to be a detection hole is provided therebelow. The conductive layer processed into the second electrode 134 may be formed using the same material and the same method as the conductive layer processed into the first electrode 132. The second electrode 134 is elongated and provided along the diameter of the detection hole to be later formed. The second electrode 134 is, for example, processed to have a length half the diameter of the detection hole. Hereupon, the first electrode 132 and the second electrode 134 may be collectively provided across the detection hole, and the lengths of the first electrode 132 and the second electrode 134 is not necessarily half the diameter of the detection hole. Further, reinforcement may be provided as necessary as in the first electrode 132.

Further, the gate electrode like, of the first electrode 132 and the second electrode 134 desirably formed as smoothly as possible when viewed from above. When the first electrode 132 and the second electrode 134 are formed into shapes without corners, generation of dust is reduced and cracks resulting breakage can be reduced. Note that in a top view of FIG. 9A, the insulating substrate 101, the base layer 102, the gate insulating layer 105, the insulating layer 125, the conductive layer 129, and insulating layer 130 are omitted.

Figure 10A:
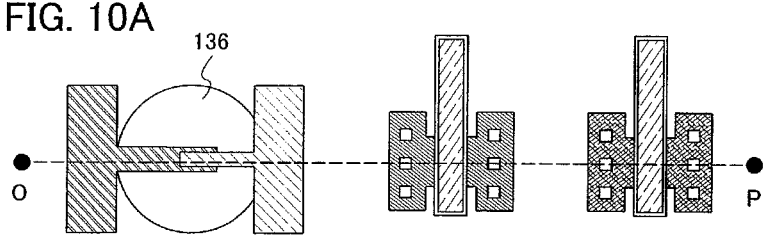
FIGS. 10A and 10B are figures illustrating a manufacturing step of a detection unit of the present invention.
Figure 10B:
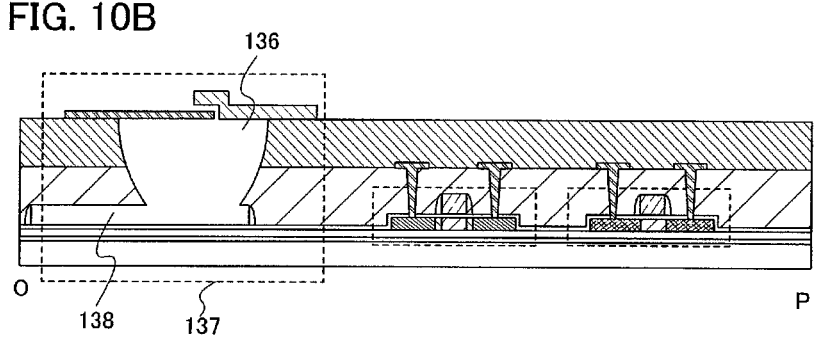

As shown in FIGS. 10A and 10B, the insulating layer 125 and the insulating layer 130 are processed to form a detection hole 136 under the first electrode 132 and the second electrode 134. Specifically, the first electrode 132 and the second electrode 134 are formed over the detection hole 136, namely, over a path of air flow flowing into an opening forming the detection hole. The insulating layer 125 and the insulating layer 130 are processed by photolithography, and the detection hole 136 is formed by wet etching or dry etching. In manufacturing the detection hole 136, a mask for etching (generally resist mask) is preferably tapered so that the end portion of the detection hole 136 is tapered. In the case of using dry etching, bias voltage is preferably set at a relatively high level in order to form a tapered end portion. In the case of using wet etching, an opening can be formed to have a semispherical shape, which is preferable. The shape of the detection hole 136 when viewed from above may be circular or rectangular, and the shape preferably corresponds to a detection object to be detected.

Further, the detection hole 136 has a depth such that it reaches the sacrificial layer 108, and the thicknesses of the insulating layer 125 and the insulating layer 130 may be determined so that the detection hole has a depth such that a detection object to be detected can fit in. Further, the sides of the detection hole 136 are preferably tapered or curved in order to make a detection object fit firmly.

When pollen is taken as an example of a detection object, the sizes are varied depending on the kinds of plants, in the range of about 30 nm to 50 μm and the pollen has a spherical shape. In the detection hole 136 at least a part of a pollen grain can enter in the hole. Accordingly, a detection hole having a diameter which is approximately 60% to 80% of a diameter of pollen to be detected is desirable. In addition, once adsorbed pollen is required not to be detached from the detection hole 136. This is because when detached, the number of the pollen grains cannot be counted accurately. Accordingly, the diameter of the detection hole 136 is 20 μm to 40 μm and the side has a curved shape preferably.

Further, when the first electrode 132 and second electrode 134 has a structure in which two cantilevers are in contact with each other, namely, a bridge structure; thus, a contact state can be maintained due to elasticity of the electrodes them selves. Accordingly, a continuous state is maintained. Alternatively, the first electrode 132 and the second electrode 134 contact each other by van der Waals force and weak electrostatic attraction due to capillary action in a later process of removing the sacrificial layer 108 and the sacrificial layer 133 and drying; thus, a continuous state can be maintained.

When a detection object is adsorbed to such a detection hole 136 provided under the first electrode 132 and the second electrode 134; thus, the first electrode 132 and the second electrode 134 are attached from each other.

Next, the sacrificial layer 108 and the sacrificial layer 133 are removed (FIG. 10B). The sacrificial layer 108 and the sacrificial layer 133 can be applied by wet etching or dry etching. An etchant is introduced from above the detection hole 136 or from an inlet provided suitably. For example, in the case where tungsten (W) is used for the sacrificial layer 133, the sacrificial layer 133 can be removed by being soaked in a solution in which 28% of ammonia and 31% of oxygenated water and pure water are mixed at a ratio of 3:5:2 for about 60 minutes. In the case of etching sacrificial layer with such a mixed solution, when an organic material such as polyimide or a resist is used for the insulating layer 125 or the insulating layer 130, there is a risk of low resistance to ammonia; thus, care must be taken with the treatment time or the shape after etching.

In the case where silicon (Si) is used for the sacrificial layer 108 or the sacrificial layer 133, they can be removed by wet etching using a mixed solution of HF and $HNO_3$ (preferably, $CH_3COOH$ is also added to the mixed solution), KOH, NaOH, EPW (a mixed solution of ethylenediamine pyrocatechol and water), EDP (ethylenediamine pyrocatechol), TMAH (tetraethylammonium hydroxide) or hydrazine. Alternatively, they can be removed by dry etching using $XeF_2$, a mixed gas of $SF_6$ and $C_4F_8$, or $SF_6$. Since most of such etchants can have selectivity to silicon oxide ($SiO_2$), silicon oxide is preferably used for the insulating layer 125. Further, KOH, EPW, EDP, TMAH, hydrazine has anisotropy of an etching rate depending on the plane orientation of a crystal, the crystal states of the sacrificial layer 108 and the insulating layer 125 are preferably different from each other.

In the case of using silicon oxide ($SiO_2$) for the sacrificial layer 108 and the sacrificial layer 133, they can be removed by wet etching using a mixed solution of HF and $NH_4F$, $NH_4HF_2$, or buffered hydrofluoric acid. Alternatively, they can be removed by dry etching using a mixed gas of HF and $NH_4F$, a mixed gas of $SF_6$ and $C_4F_8H_2$. A mixed solution of HF and $NH_4F$ can have selectivity to silicon (Si).

After removing the sacrificial layer 108 and the sacrificial layer 133, drying is carried out. In the drying process, the first electrode 132 and the second electrode 134 contact each other by van der Waals force and weak electrostatic attraction due to capillary action. Naturally, the first electrode 132 and the second electrode 134 can contact each other dependently on gravity or elasticity of the electrodes themselves.

The space formed after the sacrificial layer 108 is removed forms a micro channel for reducing pressure 138 to be a channel of air. When an intake unit is connected to one end of the space forming the micro channel for reducing pressure 138, the pressure in the micro channel for reducing pressure 138 can be reduced. In addition, pressure in the detection hole 136 can be reduced. An intake unit or the like is connected; thus, when generating air flowing downward from above the space forming the detection hole 136 or the micro channel for reducing pressure 138, a detection object approaching the detector is adsorbed to the detection hole 136. A detection object is stuck to the detection hole 136 due to reduced pressure or the like. The, the first electrode 132 provided in a lower part is pushed, and the first electrode 132 and the second electrode 134 are detached. Thus, whether a detection object is adsorbed to the detection hole 136 or not can be detected by reading a state where the first electrode 132 and the second electrode 134 are in contact and a state where they are detached. Pollen which is a typical detection object has spherical shape, so as to tightly block the detection hole; thus, the state where the first electrode 132 and the second electrode 134 are detached can easily be read. Accordingly, the shape and the size of a detection hole are determined, thereby detecting only a certain detection object. Since there are many pollen grain sizes, in order to simultaneously detect pollen grains having a first size and pollen grains having a second size, the sizes of the detection holes are differentiated.

On the other hand, even in the case of a detection object having a shape other than a spherical shape, the first electrode 132 and the second electrode 134 can be detached when the detection object partially enters into the detection hole 136.

In this embodiment mode, the formation of the detection hole 136 is carried out from the top; however, penetration etching may be carried out from the bottom. For example, the sacrificial layer 108 is exposed and removed. After that, the insulating layer 125 and the insulating layer 130 may be removed.

Thus, a microstructure 137 having the detection hole 136, the first electrode 132, and the second electrode 134 can be formed. The detection hole 136 corresponds to a detection hole 306 shown in FIGS. 4A to 4C. Specifically, a detection hole means a hole to which an object can be adsorbed, and when change in electrical resistance between a first electrode and a second electrode can be caused due to the adsorption, it can serve as a detecting element (757 shown in FIG. 2). Accordingly, the arrangement of the detection hole and the first and second electrodes, namely, the vertical relationship, is not limited to modes shown in FIGS. 10A and 10B or FIG. 2. Note that, in a top view shown in FIG. 10A, the insulating substrate 101, the base layer 102, the gate insulating layer 105, the insulating layer 125, the conductive layer 129, and the insulating layer 130 are omitted.

Figure 17:
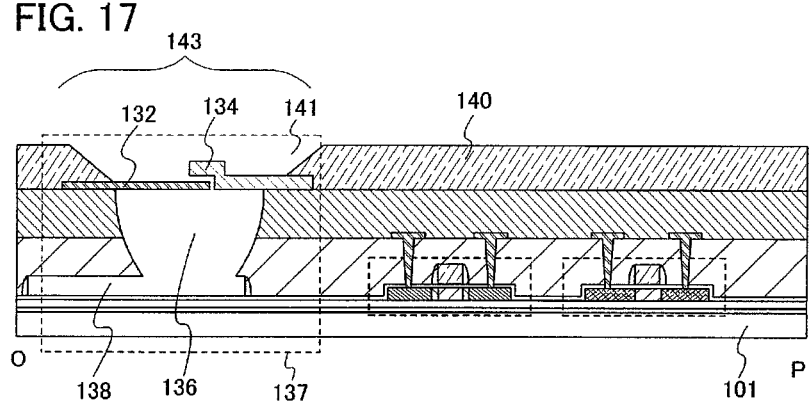
FIG. 17 is a figure illustrating a manufacturing step of a detection unit of the present invention.

Further, as shown in FIG. 17, an insulating layer 140 having a second detection hole 141 may be provided to cover end portions of the first electrode 132 and the second electrode 134. The insulating layer 140 can be manufacture in a similar manner to the insulating layer 125. With such a structure, the first detection hole 136 to which an object is adsorbed and the second detection hole 141 provided so as to overlap with the first detection hole 136 for introducing the object can serve as a detection hole 143. Thus, a plurality of detection holes may be provided. In addition, in the case of providing a plurality of detection holes, the detection holes are not required to be stacked, and they are placed so that airflow is generated through the detection hole for introducing objects and the detection hole capable of adsorption.

The microstructure 137 of the invention can be formed from a thin film material over an insulating substrate, so that cost can be reduced. In particular, in the case of using an insulating substrate has a rectangular shape, more microstructures can be obtained compared with the case of using a circular silicon wafer for the formation.

Further, an element having the detection hole and an element forming an intake unit may be simultaneously formed over one substrate. In this case, mass productivity can be improved compared to the structure in which an element forming the intake unit is formed separately and electrically connected to the detection hole.

Note that this embodiment mode can be implemented in any combination with the above embodiment modes.

Embodiment Mode 7

As a silicon layer in the invention, a crystalline silicon layer, an amorphous silicon layer, or the like can be used. In this embodiment mode, the case of using a crystalline silicon layer for a semiconductor layer 104 will be described.

Figure 15A:
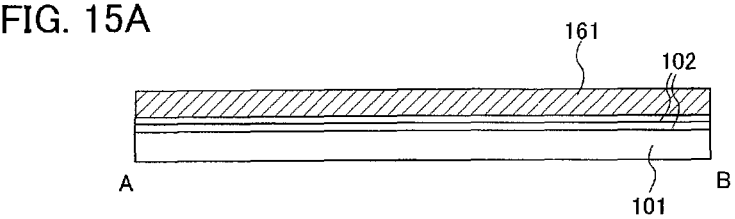
FIGS. 15A to 15D are figures illustrating manufacturing steps of polycrystalline silicon of the present invention.

First, as shown in FIG. 15A, an amorphous silicon layer 161 is formed over a base layer 102 which is a surface on which a semiconductor layer is to be formed. The amorphous silicon layer 161 can be manufactured by CVD using a material gas such as $SH_4$ or Ar.

Then, the amorphous silicon layer is crystallized by heat treatment, thereby obtaining a crystalline silicon layer. Heat treatment may be performed by laser irradiation, heating using a heating furnace, irradiation with light emitted from a lamp (hereinafter referred to as lamp annealing), or a combination of thereof.

In the case of using laser irradiation, a continuous wave laser beam (hereinafter referred to as a CW laser beam) or a pulsed laser beam may be used. As a laser beam, a laser beam emitted from one or more of the following can be used: an Ar laser, a Kr laser, an excimer laser, a YAG laser, a $Y_2O_3$ laser, a $YVO_4$ laser, a YLF laser, a $YAlO_3$ laser, a glass laser, a ruby laser, an alexandrite laser, a Ti: sapphire laser, a copper vapor laser, and/or a gold vapor laser. When a fundamental wave of such a laser beam or one of the second to fourth harmonics of the laser is used, crystals with a large grain size can be obtained. For example, the second harmonic (532 nm) or the third harmonic (355 nm) of an Nd: $YVO_4$ laser (fundamental wave of 1064 nm) can be used. In this case, power density of a laser as high as about 0.01 $MW/cm^2$ to 100 $MW/cm^2$ (preferably, 0.1 $MW/cm^2$ to 10 $MW/cm^2$) is required. The scanning rate is set at about 10 cm/sec to 2000 cm/sec to irradiate the semiconductor film.

Note that a fundamental wave of a CW laser beam and a high harmonic of a CW laser beam may be used for irradiation, or a fundamental wave of a CW laser beam and a high harmonic of a pulsed laser beam may be used for irradiation. By using a plurality of laser beams for irradiation in this manner, the energy can be compensated.

It is also possible to use a laser beam at a repetition rate that allows the laser beam of a next pulse to be applied after a silicon layer is melted by a previous laser beam and before it is solidified. By emitting a laser beam at such a repetition rate, crystal grains which have grown continuously in the scan direction can be obtained. A specific repetition rate of the laser beam is 10 MHz or more; a frequency band of significantly high frequencies compared with a frequency band of several dozen Hz to several hundred Hz, which is normally used, is used.

In the case of alternatively using a heating furnace for the heat treatment, the amorphous silicon layer is heated at 400° C. to 550° C. for 2 to 20 hours. At this time, it is preferable to set temperatures at multiple stages in the range of 400° C. to 550° C. so that the temperature becomes gradually higher. By a low-temperature heating process at about 400° C. at the initial stage, hydrogen or the like comes out of the amorphous silicon layer. Therefore, the surface roughness of the film due to crystallization can be reduced.

Further, when crystallization is performed using a metal which promotes crystallization, the heating temperature can be lowered. For example, when heating is performed after forming nickel (Ni) over the amorphous silicon layer, the heating temperature is lowered. As such a metal, there are iron (Fe), ruthenium (Ru), rhodium (Rh), palladium (Pd), osmium (Os), iridium (Ir), platinum (Pt), copper (Cu), gold (Au), and the like.

In addition to the heat treatment, the aforementioned laser irradiation may be performed to form the crystalline silicon layer.

Figure 15B:
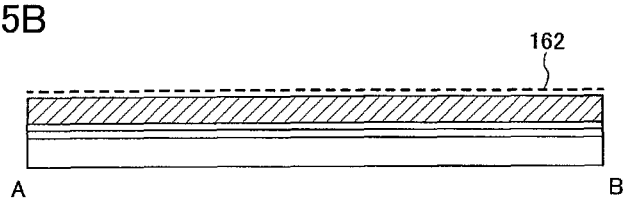

In this embodiment mode, a solution 162 containing nickel is applied to the amorphous silicon layer 161 as shown in FIG. 15B, and then crystallization is performed by using a heating furnace. The heating temperature is set at 500° C. to 550° C.

Figure 15C:
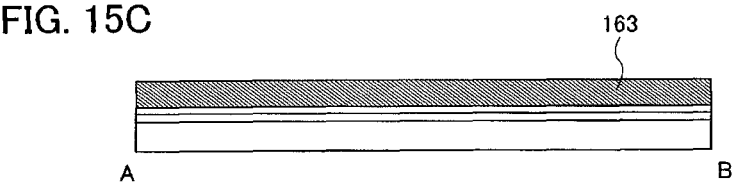

Then, as shown in FIG. 15C, a silicon layer (polycrystalline silicon layer) 163 formed by crystallization using a metal can be obtained.

Figure 15D:
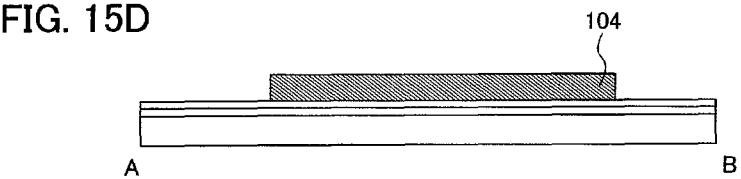

After that, the polycrystalline silicon layer is processed as shown in FIG. 15D, thereby the semiconductor layer 104 having a predetermined shape can be formed. The polycrystalline silicon layer can be processed by forming a mask using photolithography and then processing the polycrystalline silicon layer by etching using the mask to form the semiconductor layer 104.

Thus, polycrystalline silicon having a continuous crystal grain boundary can be formed by crystallization using a metal. Unlike the polycrystalline silicon which is obtained by crystallization without using a metal, the polycrystalline silicon which has a continuous crystal grain boundary will have no covalent bond cleavage at a crystal grain boundary.

In the case of using nickel for the metal, nickel silicide is formed in the silicon layer depending on the concentration of the nickel. When silicide is formed using a metal for crystallization, contact resistance can be reduced.

Such a silicide can also be formed of tungsten, titanium, molybdenum, tantalum, cobalt, or platinum other than nickel. In the case of using such a metal, a tungsten silicide layer, a titanium silicide layer, a molybdenum silicide layer, a tantalum silicide layer, a cobalt silicide layer, or a platinum silicide layer is formed. Among such metals, cobalt or platinum can be used as a metal for lowering the heating temperature of crystallization. As described above, in the case of performing crystallization using a metal, crystallization can be performed at a lower temperature as compared with the crystallization without using a metal. Therefore, the selection range of materials which can be used for an insulating substrate can be broadened. For example, in the case of crystallizing a silicon layer only by heating, heating is required to be performed at a temperature of about 1000° C. for about 1 hour, and therefore, a glass substrate which has low resistance to heat cannot be used. However, when crystallization is performed using a metal as in this embodiment mode, a glass substrate or the like which has low strain point can be used.

The case of applying polycrystalline silicon obtained by crystallization using a metal to the semiconductor layer 104 has been described above. However, the polycrystalline silicon layer may be used as a sacrificial layer. Further, the polycrystalline silicon layer can be made conductive by adding thereto a conductive material such as Ni. Accordingly, polycrystalline silicon obtained by crystallization using a metal may be used for the first electrode 132 or the second electrode 134. The detection hole 136 is provided under the first electrode 132 and the second electrode 134, and the first electrode 132 and the second electrode 134 are required to be flexible in order to keep the electrode shapes. Polycrystalline silicon obtained by crystallization using metal has a continuous grain boundary so that it has high flexibility, which is preferable.

Note that this embodiment mode can be implemented in any combination with the above embodiment modes.

This application is based on Japanese Patent Application serial No. 2005-246554 filed in Japan Patent Office on Aug. 26 in 2005, the entire contents of which are hereby incorporated by reference.

What is claimed is:

1. A method for manufacturing a semiconductor device, comprising:
    forming an insulating layer;
    forming a first electrode over the insulating layer;
    forming a second electrode over the insulating layer so as to overlap with a part of the first electrode without interposing an insulator between the first electrode and the second electrode; and
    forming an opening in a part of the insulating layer which is under a region where the first electrode and the second electrode partly overlap,
    wherein both the first electrode and the second electrode are formed on and in contact with a top surface of the insulating layer.

2. A method for manufacturing a semiconductor device according to claim 1, wherein the opening is formed by dry etching or wet etching.

3. A method for manufacturing a semiconductor device according to claim 1, wherein the semiconductor device is a particle detection sensor.

4. A method for manufacturing a semiconductor device, comprising:
    forming a semiconductor layer in a first region;
    forming an insulating layer in the first region and a second region;
    forming a first electrode in the second region over the insulating layer;
    forming a second electrode so as to overlap with a part of the first electrode; and
    forming an opening in a part of the insulating layer which is under a region where the first electrode and the second electrode overlap,
    wherein both the first electrode and the second electrode are formed on and in contact with a top surface of the insulating layer.

5. A method for manufacturing a semiconductor device according to claim 4, wherein the opening is formed by dry etching or wet etching.

6. A method for manufacturing a semiconductor device according to claim 4, wherein the semiconductor device is a particle detection sensor.

7. A method for manufacturing a semiconductor device, comprising:
- forming an insulating layer;
- forming a first electrode over the insulating layer;
- forming a sacrificial layer over the first electrode;
- forming a second electrode over the sacrificial layer so as to overlap with a part of the first electrode;
- forming an opening in a part of the insulating layer which is under a region where the first electrode and the second electrode overlap; and
- removing the sacrificial layer,
- wherein both the first electrode and the second electrode are formed on and in contact with a top surface of the insulating layer.

8. A method for manufacturing a semiconductor device according to claim 7, wherein the sacrificial layer is removed by dry etching or wet etching.

9. A method for manufacturing a semiconductor device according to claim 7, wherein the opening is formed by dry etching or wet etching.

10. A method for manufacturing a semiconductor device according to claim 7, wherein the semiconductor device is a particle detection sensor.

11. A method for manufacturing a semiconductor device, comprising:
- forming an insulating layer;
- forming a first electrode over the insulating layer;
- forming a sacrificial layer over the first electrode;
- forming a second electrode over the sacrificial layer so as to overlap with a part of the first electrode;
- forming an opening in a part of the insulating layer which is under a region where the first electrode and the second electrode overlap; and
- removing the sacrificial layer thereby contacting the first electrode and the second electrode,
- wherein both the first electrode and the second electrode are formed on and in contact with a top surface of the insulating layer.

12. A method for manufacturing a semiconductor device according to claim 11, wherein the sacrificial layer is removed by dry etching or wet etching.

13. A method for manufacturing a semiconductor device according to claim 11, wherein the opening is formed by dry etching or wet etching.

14. A method for manufacturing a semiconductor device according to claim 11, wherein the semiconductor device is a particle detection sensor.

15. A method for manufacturing a semiconductor device, comprising:
- forming a semiconductor layer in a first region;
- forming a conductive layer in the first region and a second region;
- processing the conductive layer thereby forming a gate electrode in the first region and forming a first sacrificial layer in the second region;
- forming an insulating layer so as to cover the gate electrode and the first sacrificial layer;
- forming a first electrode over the insulating layer;
- forming a second sacrificial layer over the first electrode;
- forming a second electrode over the second sacrificial layer so as to overlap with a part of the first electrode;
- forming an opening in a part of the insulating layer which is under a region where the first electrode and the second electrode overlap;
- removing the second sacrificial layer thereby contacting the first electrode and the second electrode; and
- removing the first sacrificial layer.

16. A method for manufacturing a semiconductor device according to claim 15, wherein the semiconductor device is a particle detection sensor.

17. A method for manufacturing a semiconductor device, comprising:
- forming a semiconductor layer in a first region;
- forming a conductive layer in the first region and a second region;
- processing the conductive layer thereby forming a gate electrode in the first region and forming a first sacrificial layer in the second region;
- forming an insulating layer so as to cover the gate electrode and the first sacrificial layer;
- forming a first electrode over the insulating layer;
- forming a second sacrificial layer over the first electrode;
- forming a second electrode over the second sacrificial layer so as to overlap with a part of the first electrode;
- forming an opening in a part of the insulating layer which is under a region where the first electrode and the second electrode overlap;
- removing the second sacrificial layer thereby contacting the first electrode and the second electrode; and
- removing the first sacrificial layer thereby forming a connection hole.

18. A method for manufacturing a semiconductor device according to claim 17, wherein the semiconductor device is a particle detection sensor.

19. A method for manufacturing a semiconductor device, comprising:
- forming an insulating layer;
- forming a first electrode over the insulating layer;
- forming a second electrode over the insulating layer so as to overlap with a part of the first electrode without interposing an insulator between the first electrode and the second electrode; and
- forming an opening in a part of the insulating layer which is under a region where the first electrode and the second electrode partly overlap,
- wherein both the first electrode and the second electrode are formed on and in contact with a top surface of the insulating layer, and
- wherein the first electrode and the second electrode are not in contact with each other.

20. A method for manufacturing a semiconductor device, comprising:
- forming an insulating layer;
- forming a first electrode over the insulating layer;
- forming a second electrode over the insulating layer so as to overlap with a part of the first electrode without interposing an insulator between the first electrode and the second electrode; and
- forming an opening in a part of the insulating layer which is under a region where the first electrode and the second electrode partly overlap,
- wherein both the first electrode and the second electrode are formed on and in contact with a top surface of the insulating layer, and
- wherein the first electrode and the second electrode are in contact with each other.

* * * * *